United States Patent [19]

Harrison et al.

[11] Patent Number: 5,508,045
[45] Date of Patent: Apr. 16, 1996

[54] METHOD AND AGENTS FOR CONTROL AND MANAGEMENT OF LABOR DURING PREGNANCY

[75] Inventors: Michael R. Harrison, San Francisco; Russell W. Jennings, Pacifica, both of Calif.; Thomas E. MacGillivray, Boston, Mass.; Jeffrey R. Fineman, Mill Valley, Calif.; Michael A. Heymann, San Francisco, Calif.; Robert K. Riemer, Half Moon Bay, Calif.; Eileen S. Natuzzi, San Francisco, Calif.

[73] Assignee: The Regents of The University of California, Oakland, Calif.

[21] Appl. No.: 198,512

[22] Filed: Feb. 18, 1994

Related U.S. Application Data

[63] Continuation-in-part of Ser. No. 959,006, Oct. 9, 1992, abandoned.

[51] Int. Cl.$^6$ .......................... A61K 33/26; A61K 31/21; A61K 31/195; A61K 31/505; A61K 31/47; A61K 31/52; A61K 31/16
[52] U.S. Cl. .......................... 424/608; 514/509; 514/562; 514/258; 514/307; 514/263; 514/608; 514/565
[58] Field of Search .................................... 514/509, 258, 514/562, 307, 263, 608, 565; 424/608

[56] References Cited

PUBLICATIONS

Wheeler et al., *Chemical Abstracts*, vol. 93, No. 19, abstract #179693y, 1980, p. 60.
Stewart et al., *Chemical Abstracts*, vol. 115, No. 1, abstract #5871n, 1991, p. 579.
Cotton, D. B., et al., "Role of Intravenous Nitroglycerin in the Treatment of Severe Pregnancy–Induced Hypertension Complicated by Pulmonary Edema", Dept. Obst. & Gyn. & Anesthes., Baylor Coll. of Med., vol. 154 1:91–94 (1985).
Kanji Nakatsu and Jack Diamond, "Role of cGMP in Relaxation of Vascular and Other Smooth Muscle", Can. J. Physiol., Pharmacol vol. 67:251–262 (1989).
Altabef, K. M., et al., "Intravenous Nitroglycerin for Uterine Relaxation of an Inverted Uterus", Am. J. Obest. Gynecol, vol. 166 4:1237–1238 (1992).
Peng, A. T. C., et al., "Intravenous Nitroglycerin for Uterine Relazation in the Postpartum Patient with Retained Placenta", Anestes., vol. 71 1:172–173 (1989).
J. R. Hemstad, et al., *Anesthesiology*, Effect of Nitrous Oxide on ICP Following Cranial–Dural Closure, vol. 73, No. 3A, p. A177, Sep. 1980.
Charles Weissman, et al., *Anesthesiology*, Determination of Hyper and Hypometabolism in the Postoperative ICU Patient, vol. 73, No. 3A, p. A306, Sep. 1980.
J. Leon, et al., *Anesthesiology*, Does Nitrous Oxide Affect Cerebral Blood Flow Velocity Under Neuroleptanesthesia in Children?, vol. 73, No. 3A, p. A389, Sep. 1980.
G. B. Russell, et al., *Anesthesiology*, Hyperbaric Nitrous Oxide Anesthesia in Rats for Mac Determination, vol. 73, No. 3A, p. A399, Sep. 1980.
M. S. Pettis, et al., *Anesthesiology*, Nitrous Oxide and Coronary Artery Construction in Pigs, vol. 73, No. 3A, p. A553, Sep. 1980.
W. E. Hoffman, et al., *Anesthesiology*, Fentanyl with Nitrous Oxide Does not Alter Cerebral Autoregulation or Blood Flow Compared to Unanesthetized Rats, vol. 73, No. 3A, p. A603, Sep. 1980.
T. S. Lee, et al., *Anesthesiology*, Inotropic Effects of Nitroglycerin, nitroprusside and Trimethaphan on Isolated Rabbit Myocardium, vol. 73, No. 3A, p. A629, Sep. 1980.
M. Palot, et al., *Anesthesiology*, Effects of Nitrous Oxide and/or Halothane on Clevage Rate During General Anesthesia for Oocyte Retrieval, vol. 73, No. 3A, p. A930, Sep. 1980.
M. Yaster, et al., *Anesthesiology*, Interaction of Fentanyl and Nitrous Oxide on Cerebral and Peripheral Hemodynamics in Newborn Lambs, vol. 73, No. 3A, p. A1117, Sep. 1980.
D. O. Warner, et al., *Anesthesiology*, Nitrous Oxide Stimulates Expiratory Muscles in Dogs, vol. 73, No. 3A, p. 1172, Sep. 1980.
U. Pandit, et al., *Anesthesiology*, Nitrous Oxide Does Not Increase Postoperative Nausea/Vomiting in Pediatric Outpatients Undergoing Tonsillectomy–Adenoidectomy, vol. 73, No. 3A, p. A1245, Sep. 1980.
E. G. Carton, et al., *Anesthesiology*, Effects of Nitrous Oxide on Contractility and Relaxation of Isolated Mammalian Ventricular Myocardium, vol. 73, No. 3A, p. A1271, Sep. 1980.
M. J. Leroy, et al., *Biochemical Pharmacology*, Correlation Between Selective Inhibition of the Cyclic Nucleotide Phosphodiesterases and the Contractile Activity in Human Pregnant Myometrium Near Term, vol. 38, No. 1, pp. 9–15, 1989.
Hidetaka Izumi, et al., *Am. J. Obstet Gynecol.*, Gestational changes in L–arginine–induced relaxation of pregnant rat and human myometrial smooth muscle, vol. 169, No. 5, pp. 1327–1337, 1993.
Chandrasekhar Yallampali, et al., *Am. J. Obstet. Gynecol.*, An L–arginine–nitric oxide–cyclic guanosine monophosphate system exists in the uterus and inhibits contractility during pregnancy, vol. 170, pp. 175–185, 1993.
E. S. Natuzzi, *Biochemical and Biophysical Research Communications*, Nitric Oxide Synthase Activity in the Pregnant Uterus Decreases at Parturition, vol. 194, No. 1, pp. 1–8, 1993.
David S. Warner, et al., *Anesthesiology*, Nitrous Oxide Does not Alter Infaret Volume in Rats Undergoing Reversible Middle Cerebral Artery Occlusion, vol. 73, pp. 686–693, 1990.

(List continued on next page.)

Primary Examiner—Marianne M. Cintins
Assistant Examiner—William R. A. Jarvis
Attorney, Agent, or Firm—Hana Verny

[57] ABSTRACT

A method for control, management and inhibition of a preterm labor by providing to a pregnant woman a donor of nitric oxide. Management and inhibition of preterm labor is achieved by administering to a pregnant woman a nitric oxide or donor source in a safe and non-toxic concentration during the preterm labor.

15 Claims, 6 Drawing Sheets

PUBLICATIONS

Dan Lawson, et al., *Anesthesiology*, Nitrous Oxide Effects on Isolated Myocardium: A Reexamination in Vitro, vol. 73, pp. 930–943, 1990.

Christoph Lees, et al., Arrest of preterm labour and prolongation of gestation with glyceryl trinitrate, a nitric oxide donor, *The Lancet*, vol. 343, No. 8909, May 28, 1994, pp. 1325–1327.

Jeffrey S. Greenspoon, et al., Breech extraction facilitated by glyceryl trinitrate sublingual spray, *The Lancet*, vol. 338, No. 8759, Jul. 13, 1991, pp. 124–125.

Word, R. A., et al., "Effects of cGMP on $[Ca^{2+}]_i$, Myosin Light Chain Phosphorylation, and Contraction in Human Myometrium", *Am. J. Physiol.*, 260:c861–c867 (1991).

METHOD AND AGENTS FOR CONTROL AND MANAGEMENT OF LABOR DURING PREGNANCY

This is a continuation-in-part application of the application entitled "Uterine Contracting and Relaxing Compositions and Methods for Prolonging Labor and Terminating Pregnancy", Ser. No. 07/959,006, filed on Oct. 9, 1992, now abandoned.

BACKGROUND OF THE INVENTION

1. Field of the Invention

This invention concerns a method and agents for control, management and inhibition of a preterm labor or for inducing labor in overterm pregnancy by providing to a pregnant woman or pregnant mammal a donor or inhibitor of nitric oxide alone or in combination with other enhancing or modulating agents. In particular, this invention concerns a method for management and inhibition of preterm labor by administering to a pregnant woman a nitric oxide source in a safe and non-toxic concentration during the preterm labor or a nitric oxide inhibitor during the overterm pregnancy.

2. Background and Related Disclosures

Spontaneous preterm labor during pregnancy remains an enormous, and apparently increasing problem confronting the medical community. Only few advances have been made in the understanding of causes of preterm labor, in the early detection of preterm labor and in its general management. Major advances so far have occurred in fetal and neonatal care ameliorating or preventing pathophysiological consequences to the prematurely born infant. However the ability to definitely and safely stop preterm labor and thereby to allow a pregnancy to advance towards term has thus far eluded the medical and scientific community.

In humans, the maintenance of pregnancy as well as onset of labor appears to depend on multiple factors. Normal progression of pregnancy until the term requires relaxation of uterine smooth muscle until parturition, but the mechanism that maintains uterine relaxation during pregnancy is unknown. Normal parturition typically begins with labor. Labor consists of a series of rhythmic, progressive contractions of the uterus that cause effacement and dilation of the uterine cervix. In normal pregnancy, labor usually begins within two weeks before estimated delivery.

Diagnosis of spontaneous preterm labor is made upon the onset of labor when regular uterine contraction are accompanied by progressive cervical dilation and/or effacement before 37 week of gestation. If the preterm labor is let to continue unhindered it results in preterm delivery. Preterm delivery accounts for a major proportion of perinatal deaths and significant proportion of postnatal and childhood defects and therefore, maintaining the fetus in utero is preferred to allowing preterm delivery.

Preterm labor, whether occurring spontaneously or the one which invariably follows any significant transuterine fetal manipulation from needle puncture to fetoscopy to hysterotomy for fetal surgery, presents a serious problem and in later case has proven to be a limiting factor for all types of fetal intervention. The very severe form of spontaneous preterm labor or labor induced by an incision in the gravid uterus for open fetal surgery is resistant to all known forms of tocolysis attempted both experimentally and clinically over the last decade. Indeed the management of preterm labor after fetal surgery is particularly difficult and dangerous for mother and fetus because aggressive treatment with magnesium sulfate, betamimetics and other hemodynamically-active tocolytic agents has resulted in sequelae for both mother and fetus.

Once preterm labor is diagnosed, the risks and benefits of labor inhibition must be weighed against those of allowing delivery to occur. The risks from labor inhibition are primarily related to the side effects of the labor inhibiting drugs. Once preterm labor is diagnosed and the gestational age is established as appropriate for labor inhibition, contraindications such as eclampsia, preeclampsia, ruptured placenta, dead or anomalous fetus, fetal distress or chorioammionitis to premature delivery is determined and the particular available tocolytic agent is selected. Until now, tocolytic agents most often used to inhibit preterm labor are $\beta$-adrenoreceptor stimulants such as epinephrine or its synthetic analogs and derivatives salbutamol, terbutaline, isoxsuprine, ritodrine, and fenoterol, magnesium sulfate, prostaglandin inhibitors such as aspirin indomethacin and naproxen, ethanol and calcium channel-blocking agents such as nipedifine or nicardipine. However, the potential adverse effects of these drugs limit their use.

Patients undergoing hysterotomy and fetal surgery typically experience difficulty with preterm labor despite treatment involving a regimen of preoperative indomethacin, intraoperative deep halogenated inhalation anesthesia, and postoperative indocin, magnesium sulfate, and betamimetics. The majority of these patients has visible and palpable intraoperative uterine contractions often associated with fetal bradycardia from cord compression. These intraoperative contractions respond erratically to deepening anesthesia and to acute administration of magnesium sulfate or terbutaline. All the patients have significant labor postoperatively which in mild form can be controlled by intravenous tocolytics administered during several days, but in severe form can take a week or longer to control with intravenous medication before they could be weaned to oral or subcutaneous pump medication. All patients undergoing hysterotomy eventually develop uncontrolled preterm labor, premature rupture of membranes, and premature delivery from 27–34 weeks gestation.

It is clear that even the best tocolytic regimen available currently is unsatisfactory for prevention or inhibition of preterm labor. Additionally to proving ineffective, such standard tocolytic regimen had potentially serious harmful effects on both mother and fetus. Halogenated inhalation anesthesia needed to achieve uterine relaxation had been shown to produce significant myocardial depression in both mother and fetus, the indomethacin produces constriction of the fetal ductus arteriosus, and serial echocardiograms in patients demonstrated that ductal constriction producing tricuspid regurgitation can lead to significant right-heart failure in the fetus. Perhaps even more important, indomethacin tocolysis has recently been shown to be associated with an increased risk of perinatal intracranial hemorrhage in the neonate. Finally, it is becoming obvious that the aggressive treatment of postoperative labor with maximal doses of magnesium and betamimetics is quite toxic for the mother and attempts to avoid maternal pulmonary edema in this clinical setting led to maternal hypovolemia with documented reversal of diastolic flow in the uterine arteries. It, therefore, appears that currently available tocolytic treatment has significant potential to harm the fetus.

Different pharmacological approaches using the above tocolytic drugs have been tried to control preterm labor, but even ritodrine which has been specifically synthesized for use in obstetrics and gained wide general acceptance and application, has now come under significant scrutiny and its effectivity and safety is being questioned. A major underlying cause for this lack of effective treatment of preterm labor is insufficient information on the basic physiology of uterine smooth muscle and therefore the inability to formulate therapeutic strategies based on a true understanding of the mechanisms involved.

The study of preterm labor and discovery of new approaches toward prevention, management and treatment of preterm labor is therefore extremely desirable.

Nitric oxide (NO) is a free radical with a very short half-life. Nitric oxide is synthesized from the amino acid L-arginine by the nitric oxide synthase (NOS). So far, the only clearly established role for nitric oxide is as a cytotoxic molecule for invading microorganisms and tumor cells. However, other physiological activity, such as acting as a neurotransmitter in the brain and in the periphery, affecting GI tract motility and penile erection were also observed. Nitric oxide is produced in vascular endothelial cells by the nitric oxide synthase and seems to mediate vascular smooth muscle relaxation by increasing levels of cGMP. Its effect on relaxation of intrapulmonary artery and vein was described in *J. Pharmacol. Exp. Ther.*, 228:33–42 (1984).

Nitric oxide, its physiology, pathophysiology and pharmacology is described in *Pharmacological Reviews*, 43:109–134 (1991). While there were some in vitro studies described in *Brit. J. Pharmacol.*, 34:604–612 (1968) concerning the effect of nitric oxide precursors on animal isolated uterus, such studies did not lead to any conclusion or advancement useful for control of labor, particularly preterm labor in human or mammal pregnancy.

It would be therefore highly advantageous to provide a method and agents which would, in a rational and reproducible way, control, manage and inhibit preterm labor or, when applicable, induce labor in late pregnancies when such induction of labor is indicated.

The current invention provides a method and agents which enable clinicians to control, manipulate or inhibit preterm labor or induce labor in late pregnancies in safe and reproducible way. The method gives a clinician control over the labor progression until now unavailable, by administering to a pregnant woman nitric oxide source or inhibitors, alone or in a suitable combination with other agents and with pharmaceutically acceptable excipients. Such treatment has not been heretofore available.

All patents and publications cited herein are hereby incorporated by reference in their entirety.

SUMMARY

One aspect of the current invention is a method for controlling and managing spontaneous or surgically induced preterm labor or for inducing labor in overterm pregnancy.

Another aspect of the current invention is a method for controlling and managing preterm labor by administering to a pregnant woman an exogenous donor or source of nitric oxide in order to maintain uterine quiescence and to prevent or inhibit and control preterm labor.

Yet another aspect of the current invention is a method for control, management and inhibition of preterm labor by manipulating levels of nitric oxide synthase.

Still another aspect of the current invention is a method for controlling and managing preterm labor or inducing labor in overterm pregnancy by administering to a pregnant woman compounds which alter nitric oxide availability.

Still yet another aspect of the current invention are agents which produce control or alter nitric oxide availability useful for control and inhibition of preterm labor or for induction of labor in overterm pregnancy.

Yet another aspect of the current invention are pharmaceutical compositions comprising agents which produce, control or alter nitric oxide availability or manipulate the level of nitric oxide synthase, or which inhibit or slow down the breakdown of the substance in the muscle cells, guanosine 3':5'-cylic monophosphate (cGMP), which is produced by the action of the nitric oxide and which is eventually responsible for the muscle relaxation, which compositions are useful for control of preterm labor or for induction of labor in overterm pregnancy and which compositions are administered to a pregnant woman alone or in combination with other pharmaceutically effective agents which potentiate nitric oxide action.

DEFINITIONS

Figure 1:
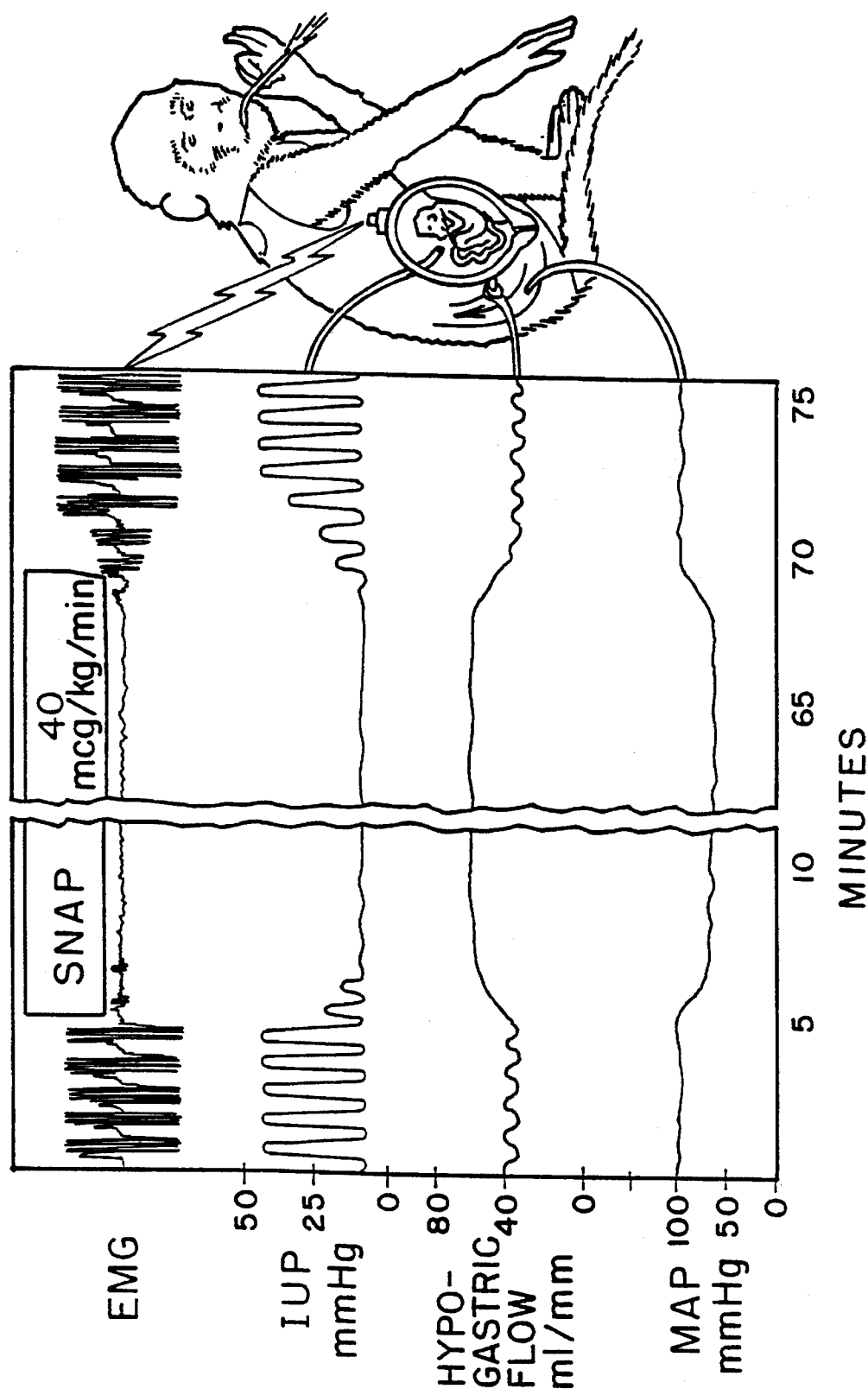
FIG. 1 is a schematic strip chart recording obtained from pregnant rhesus monkey demonstrating ablation of preterm labor after administration of nitric oxide donor S-nitroso-N-acetyl penicillamine (SNAP).
Figure 2A:
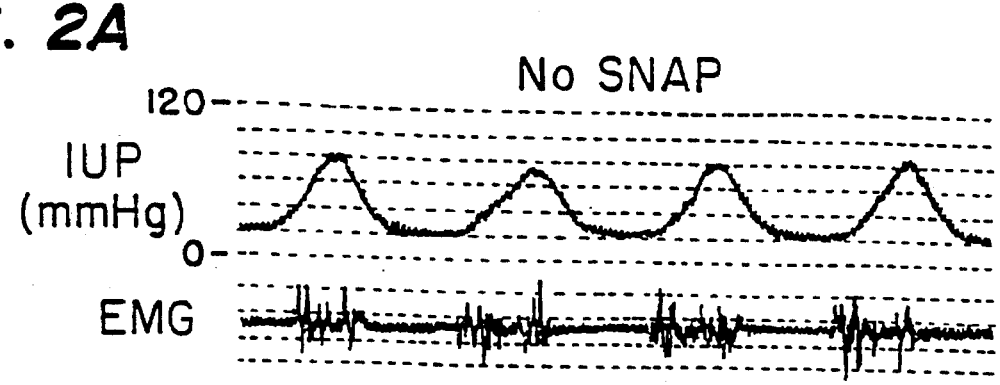
FIGS. 2A, 2B, 2C and 2D show is a dose response graph representing intrauterine pressure (IUP) and uterine electromyogram (EMG) of pregnant rhesus monkey experiencing preterm labor contractions in response to various doses of SNAP compared to a IUP and EMG response observed in control pregnant rhesus monkey having been given no medication.
Figure 2B:
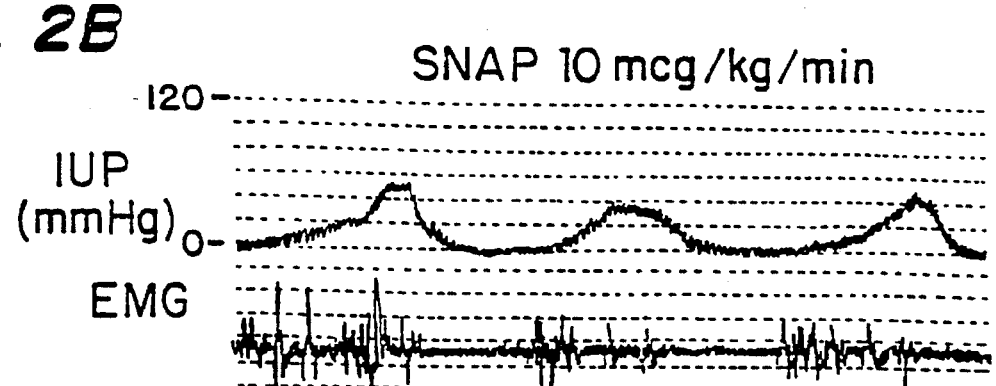
Figure 2C:
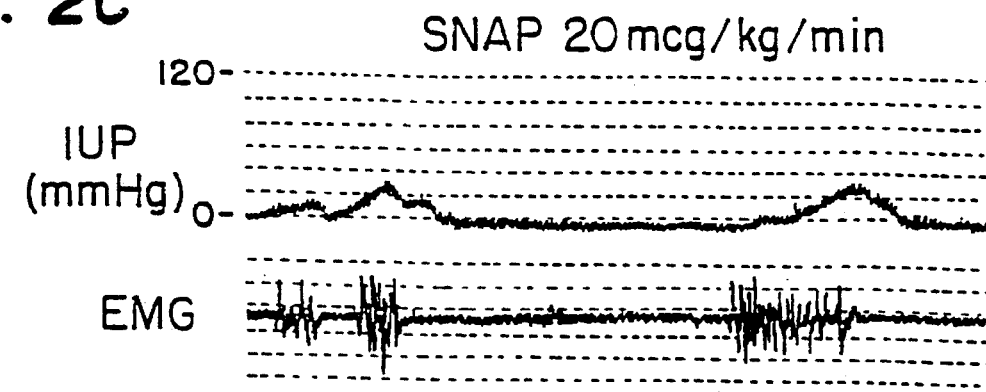
Figure 2D:
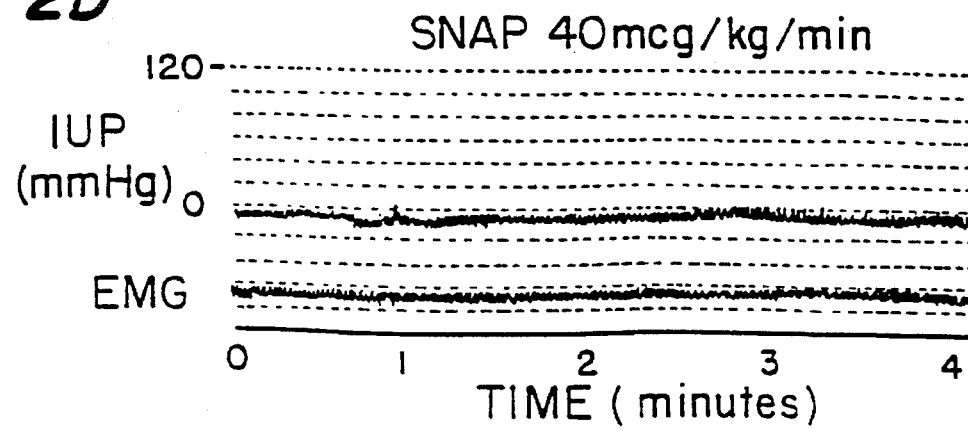

As used herein, the term:

"Nitric oxide source" means nitric oxide donor or precursor capable of potentiating the effect, or increasing the level of nitric oxide in utero and include but are not limited to S-nitroso-N-acetylpenicillamine (SNAP) and analogues thereof, nitric oxide nucleophiles or nitric oxide adducts such as diethylamino/nitric oxide (DEA/NO), DETA/NO or spermine or other nucleophilic groups known in the art, nitroglycerin and analogues thereof such as isosorbide dinitrate, nitropaste, nitropatches, nitroprusside and analogues thereof, other nitrovasodilators such as hydroxylamine, sodium azide, 2-isosorbide mononitrate, PETN, and analogues thereof, endogenous precursors of nitric oxide such as L-arginine, metabolic precursors of L-arginine.

"Nitric oxide synthase inhibitor" means a compound which is effectively able to prevent the nitric oxide synthase mediated production of nitric oxide from L-arginine, by competing with L-arginine as the substrate for the nitric oxide synthase and thus preventing nitric oxide production and include but are not limited to compounds such as $N^{107}$-nitro-L-arginine (N-NA), $N^{\omega}$-nitro-L-arginine methyl ester (L-NAME), $N^{\omega}$-mono-methyl-L-arginine (L-NMMA).

DETAILED DESCRIPTION OF THE INVENTION

This invention generally concerns a method and agents for control, management and manipulation of labor during pregnancy. The method is particularly useful for inhibition of spontaneous preterm labor which would, if untreated, result in premature delivery or abortion and for inhibition of surgically induced labor during transuterine fetal surgery. The method is also useful for inducing the labor in overterm pregnancies where the labor does not occur on term and when it is necessary to induce labor in order to assure the normal delivery.

The current method comprises administration to a pregnant woman who experiences preterm labor, particularly labor which occurs before 37th week of gestation, a therapeutically effective amount of a nitric oxide donor or source, alone or in combination with other pharmaceutically effective agents which may enhance or otherwise modulate the effect of nitric oxide donors or sources. Effect of these compounds on preterm labor was studied in vivo, in vitro and in clinical setting.

I. Method for Treatment and Prevention of Preterm Labor

The present invention provides a novel method for control, treatment, management and prevention of preterm labor. The method comprises administering to a pregnant woman experiencing preterm labor before the 37 week of gestation, or to a mammal female experiencing preterm labor, a composition consisting essentially of a donor or a source of nitric oxide, alone or in combination with a uterine relaxant selected from the group consisting of agents capable of potentiating the effect, or increasing the level, of nitric oxide in utero in an amount effective to inhibit or counter the onset of uterine contractions. Such agents include but are not limited to nitric oxide donors such as for example, S-nitroso-N-acetylpenicillamine, nitric oxide nucleophiles and adducts, nitroglycerin, hydroxylamine, sodium azide, and diethylamino nitric oxide and other analogs thereof, and precursors such as L-arginine.

The discovery that nitric oxide level can manipulate contractions has definite implications for the clinical management of preterm labor and its consequences. The early detection of the advent of preterm labor permits intervention to stop or retard preterm labor occurring at an undesirable early time.

This invention concerns a discovery that nitric oxide is a powerful mediator of uterine smooth muscle relaxation. Exogenously supplied nitric oxide was found to stop or ablate even well established preterm labor. The invention provides a way of regulating the levels of nitric oxide in utero by means of agents acting upon the nitric oxide or its enzyme nitric oxide synthase. Some of the present agents are useful to retard preterm labor, and others to induce labor leading to delivery or abortion.

The method was studied in in vivo rhesus monkey model specially developed for this purpose, in in vivo sheep, in in vitro pregnant rat uterine tissue, in mouse uterine monocytes and also in controlled clinical settings. Results of all these studies provide evidence that the administration, preferably by intravenous infusion, of compound which is either a donor, source or a precursor of nitric oxide effectively suppresses the virulent uterine contractions appearing either spontaneously in a pregnant woman as preterm labor or which were induced by surgical manipulation of the uterus. Infusion of the nitric oxide donor or substrate suppressed and even ablated preterm labor or induced contractions. Administration of these agents induced changes in uterine contractility through levels of nitric oxide. Infusions of normal saline or other control agents had no effect either on contractility or on maternal hemodynamics.

In one embodiment, the current invention provides uterine relaxing composition comprising a nitric oxide donor capable of increasing or maintaining levels of nitric oxide in uterus and in this way controlling, inhibiting, managing and regulating preterm labor.

II. Method for Induction and Augmentation of Uterine Contractions

The present invention additionally provides a method for the induction and augmentation of uterine contractions. By decreasing the levels of nitric oxide or by administering nitric oxide inhibitors, uterine contractions can be effectively induced.

Thus, in another embodiment, the present invention provides a uterine contracting composition, comprising a uterine contracting agent capable of countering the effect, or reducing the level of nitric oxide, and optionally a second agent selected from the group consisting of other anti-gestational agents, anesthetics, analgesics, and mixtures thereof.

This method can be effectively used to induce labor and contraction in overterm pregnancies when the labor induction is indicated. In such a case, nitric oxide level is decreased by administration of nitric oxide inhibitors alone or in combination with other agents.

III. In Vivo Studies

The role of nitric oxide in control of labor and contractions was studied in a clinically relevant monkey and sheep models.

One of the primary limitations of research on preterm labor is the absence of a suitable experimental model. Up to the present time, the unpredictable nature of preterm labor in humans and animals had made its systematic study difficult. For the purposes of this invention, the non-human primate animal models similar to the human system, and the sheep model were developed. Experimental tests performed in primates and in other high mammals, permitted a simple extrapolation of the invention utility, applications and regimes to humans.

Both the primate and sheep models were used to study the mechanism by which nitric oxide mediates uterine relaxation, the role of endogenous nitric oxide production in pregnancy, the role of exogenously administered drugs that increase the level of nitric oxide, as well as their combination with other agents to determine their efficacy in the treatment of preterm labor, the timing and route of administration for clinical use, and adverse or long-term effects of these drugs on the mother and fetus or neonate.

One form of induction of preterm labor, which was observed in over 400 fetal surgical procedures in non-human primates is labor induced by hysterotomy, an incision of the uterus. In monkeys, as in humans, mid- to late-gestational hysterotomy reliably induces labor. This labor occurs 100% of the time, is difficult to control with standard tocolytic regimens, and has a predictable course lasting 5–7 days. Hysterotomy induced preterm human labor corresponds to spontaneously occurring preterm labor, and therefore, provides a unique opportunity to study labor. When combined with sensitive methods to detect, monitor, and quantitate preterm labor, the monkey hysterotomy model provides a reproducible model which is representative of post-hysterotomy preterm labor in humans.

Because of its smooth muscle relaxation activity observed before in other tissues, nitric oxide was studied for its mediating activity in uterine smooth muscle relaxation on the primate model having induced preterm labor by hysterotomy.

Eleven time-mated pregnant rhesus monkeys (Macaca mulatta), having gestational age from 106 to 137 days, and expected term at 165 days were equipped and accustomed to a vest suitable to be worn in awake state and to cover and protect various sensors, tubings, catheters and probes implanted into the monkey uterus. The schematic chart of implanted sensors and probes is shown in FIG. 1 which also illustrates the ability to continuously monitor the uterine muscular activity and contractions by electromyograph (EMG), intrauterine pressure (IUP), hypogastric flow and maternal mean arterial pressure (MAP).

Prior to initiation of studies, monkeys were premedicated with atropine 0.02 mg/kg and ketamine 10 mg/kg given by intramuscular injection (IM) and anesthetized with 1.5% isofluorane for placement of monitoring catheters, flow probes, and radiotelemeter for electromyogram. Polyvinyl fluid-filled catheters for pressure transduction were placed in the maternal common femoral artery and vein, the hypogastric artery, and the intraamniotic activity. An ultrasonic flow probe was placed around the left hypogastric artery to measure uterine blood flow. A polyvinyl catheter in the common femoral vein was used for infusions. All catheters were tunneled subcutaneously to the back where they exited into a vest and steel tether system. A radiotelemeter with two electrodes placed 1 cm apart on the uterine fundus and a fluid-filled pressure catheter placed through the myometrium into the amniotic space continuously transmitted the uterine electromyogram (EMG) and the intrauterine pressure (IUP). All data were continuously displayed and stored on a strip chart recorder. Postoperatively, when the monkeys recovered they were returned to their cages so they could be studied in a chronic, awake state. The monkeys received oxymorphone 0.15 mg/kg IM every 8 hours and cephalexin 15 mg/kg by intravenous infusion twice daily. Monkeys were handled in accordance with a protocol approved by the Committee on Animal Research. Detailed protocol of the monkey model is described in Example 1.

In these studies, it was observed that maternal laparotomy and uterine manipulation for placement of monitors and catheters consistently initiated uterine irritability which, in all monkeys, progressed to organized labor over several days, usually worse at night. When no tocolytic therapy was given, labor progressed until membrane ruptured and the fetus was delivered. As labor progressed, the uterine EMG tracings evolved from diffuse random spikes associated with small increases in intrauterine pressure into organized, fusiform shaped complexes associated with high-amplitude pressure increases. As expected, uterine blood flow decreased during contraction resulting in increased maternal arterial pressure.

Typically, the vested monkey had surgically induced preterm labor according to Example 1 and was then treated with compounds that alter nitric oxide availability.

In four monkeys, nitric oxide source was administered by intravenous infusion of S-nitroso-N-acetylpenicillamine (SNAP) dissolved in 0.9% saline (0.2 mg/ml). SNAP infusion rate (range 0.625 µg/kg/min to 40 µg/kg/min) was titrated in all monkeys to maintain maternal mean arterial blood pressure (MAP) above 60 mmHg.

FIG. 1 illustrates EMG, IUP, hypogastric flow and MAP values in one monkey experiencing severe preterm labor contractions. During the preterm labor episode, observed IUP was between 5 to about 40 mmHg and regular muscular contractions appearing in regular intervals were observed as seen on EMG portion of the chart. During the contractions, hypogastric flow oscillated around and generally was lower than 40 ml/mm. Maternal arterial pressure (MAP) increased to about 100 mmHg from the normal pressure around 60 mmHg. Administration of SNAP in concentration 40 µg/kg/min resulted in almost immediate inhibition of muscular contractions as well as in decrease of intrauterine pressure to a normal level around 5–7 mmHg. Hypogastric flow increased to about 50–60 ml/min and maternal arterial pressure decreased to close to normal levels of around 50–60 mmHg. These parameters were held constant and labor held in abeyance for the entire period when the infusion of SNAP repeatedly was administered. When the infusion of SNAP was ended around 68 minutes, the EMG, IUP, MAP and hypogastric flow levels returned to its pretreatment levels and preterm contractions returned with the same frequency and strength. These results have been observed in all treated monkeys. The strength of contractions, expressed as uterine contractility index, before and after the SNAP infusion were dose dependent. Results obtained after administering various doses are shown in Table 1.

TABLE 1

| | | | Uterine Contractility in Rhesus Monkey | | | |
|---|---|---|---|---|---|---|
| | | SNAP | INDEX | | | |
| MONKEY # | GESTATIO-NAL AGE | DOSE (µg/kg/min) | before | after | % CHANGE | OUTCOME |
| 1 | 112 d | 10 | 43 | 13 | 70 | Sacrificed |
| | | 10 | 49 | 4 | 92 | |
| | | 10 | 80 | 19 | 76 | |
| | | 10 | 82 | 31 | 62 | |
| 2 | 111 d | 5 | 49 | 29 | 41 | Sacrificed |
| | | 10 | 95 | 53 | 44 | |
| | | 20 | 84 | 31 | 63 | |
| | | 40 | 39 | 1 | 97 | |
| 3 | 128 d | 0.625 | 44 | 17 | 64 | Sacrificed |
| | | 1.25 | 59 | 18 | 70 | |

TABLE 1-continued

Uterine Contractility in Rhesus Monkey

| MONKEY # | GESTATIO-NAL AGE | SNAP DOSE (µg/kg/min) | INDEX before | INDEX after | % CHANGE | OUTCOME |
|---|---|---|---|---|---|---|
|  |  | 2.5 | 53 | 10 | 82 |  |
| 4 | 137 d | 2.5 | 73 | 51 | 31 |  |
|  |  | 5 | 55 | 30 | 46 |  |
|  |  | 10 | 62 | 20 | 68 |  |
|  |  | 20 | 71 | 14 | 80 |  |
|  |  | 20 | 90 | 50 | 45 |  |
|  |  | 40 | 90 | 20 | 78 |  |
| 5 | 139 d | None | 4 | 105 |  | Labor increased abort after 28 h |
| 6 | 111 d | None | 8 | 119 |  | Labor increased abort after 32 h |

Normal term in monkey is 165 days.

Five monkeys having induced labor by hysterotomy at gestational age as given in Table 1 were treated either repeatedly with one dose (monkey 1) where the dose of 10 µg/kg/min was repeatedly administered to monkey in labor, or with various doses (monkeys 2–4). Index before and after the treatment was determined and expressed as % of change against untreated (before) state. The monkey was first treated, then left without treatment for 30 minutes and then the treatment with the same or different dose was repeated. As seen in Table 1, each treatment of monkey 1 resulted in decrease in contractions from 62–92%. In monkeys 2–4, treated with various increasing doses of SNAP, decrease in contractions was dose dependent and varied from 31 to 97%, depending in the dose and also on the degree of contractions before the treatment was initiated.

To quantify labor, a uterine contractility index derived by integrating the area under the intrauterine pressure curve in 10 minute intervals was developed. Dose response to SNAP was determined in monkeys by calculating the percentage change in the uterine contractility index (the difference between the average contractility index during the 30 minutes of infusion and the average contractility index during the 30 minutes period immediately preceding the SNAP infusion), for varying dose of SNAP.

Table 1 also shows that in 2 untreated monkeys, preterm labor continued to abortion at 28 or 32 hours later. In treated animals, 31–97% dose dependent change in uterine contractility was observed.

In addition to SNAP, 8-bromoguanosine 3':5'-cyclic monophosphate, given as an intravenous 5-mg/kg bolus to two monkeys, showed only transient effect on contractions. Zaprinast given as an intravenous 3-mg/kg bolus to two additional monkeys, decreased contractions by about 35%.

At any time in the progression from uterine quiescence to full labor, infusion of SNAP or any other tested compound ablated the EMG and mechanical activity of the contracting uterus. FIG. 1 depicts the response to SNAP infusion on continuously recorded uterine EMG, intrauterine pressure, maternal mean arterial pressure (MAP), and hypogastric artery blood flow. The response depicted in FIG. 1 was typical and very consistent for all tested monkeys. In four monkeys, infusion of SNAP for 30 minutes (17 occasions) was always associated with a decrease in the frequency and amplitude of contractions (Table 1).

The effects of SNAP on uterine contractions were dose dependent. As SNAP infusion increased, contractions decreased in amplitude and frequency and were ultimately obliterated as seen in FIG. 2. FIG. 2 shows the dose dependency of monkey uterus contractility in a monkey experiencing severe contractions (FIG. 2A) having subsequently administered 10 (FIG. 2B), 20 (FIG. 2C), and 40 (FIG. 2D) µg/kg/min of SNAP by infusion. Control monkey received no SNAP but was injected with the same volume of saline. The uterine contractility index, which considers both amplitude and frequency of contractions, decreased with increasing doses of SNAP and ultimately prevented preterm delivery which occurred in untreated control.

As seen from FIG. 2, SNAP in 40 µg/kg/min dose was sufficient to almost completely abate the preterm labor while the SNAP dose of 20 µg/kg/min decreased the number and strength of contractions by about 75%. The lower dose 10 µg/kg/min decreased contractions by about 30%, slowing the frequency and decreasing the strength of contractions.

Figure 3:
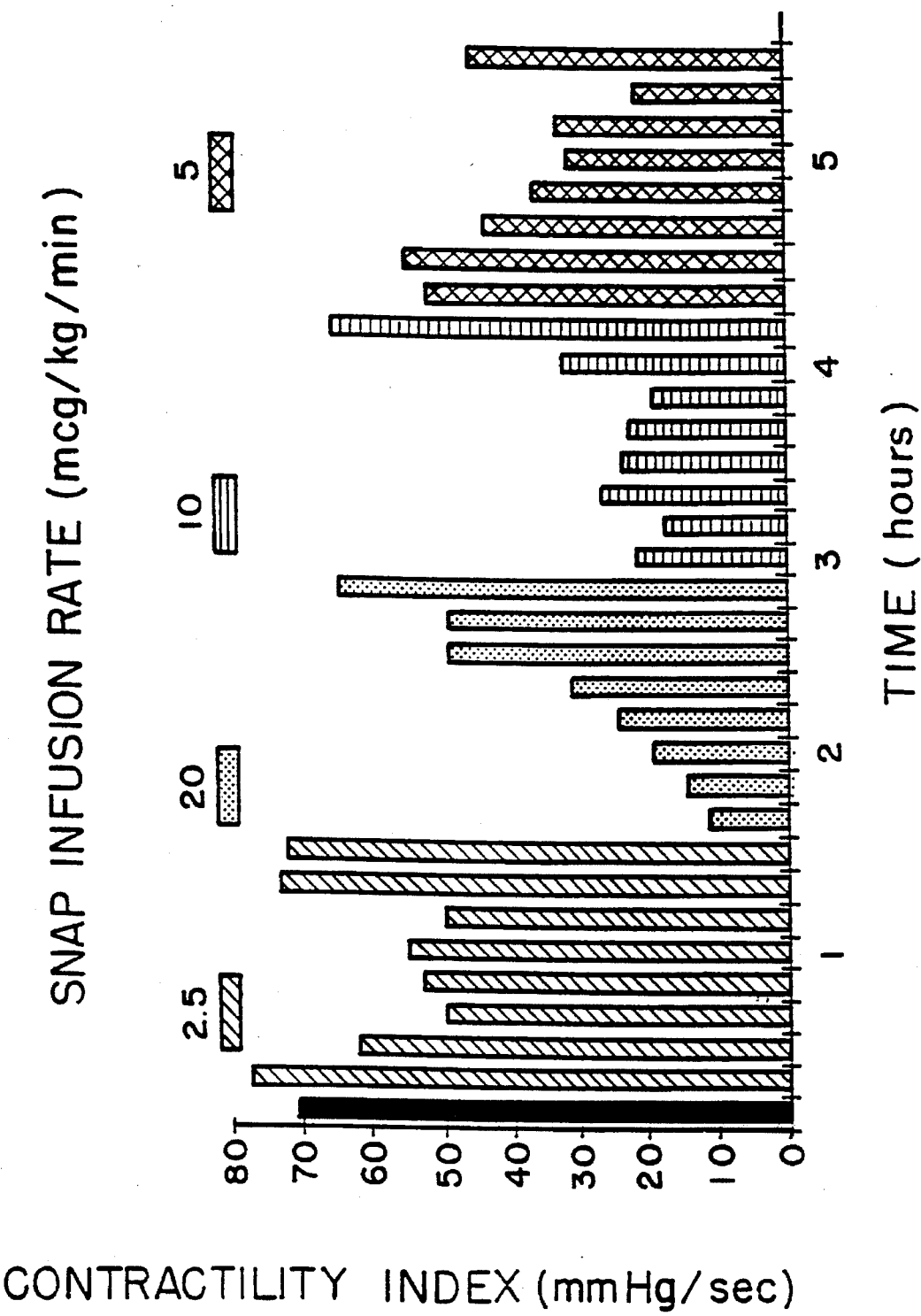
FIG. 3 depicts the dose dependent effects of SNAP infusion on preterm labor in rhesus monkey.

FIG. 3 confirms the ability of nitric oxide to inhibit or decrease contractions in dose dependent manner. In FIG. 3, one monkey experiencing contractions following hysterotomy was treated with different individual doses of SNAP over 30-minute intervals. Doses were assigned in random order. The SNAP infusion was stopped for at least 30 minutes between doses to allow the contractility index to recover. The time of actual infusion is shown as a bar with dose shown above.

The effects of SNAP infusion on preterm labor in the monkey were dose dependent. The uterine contractility index was derived by integrating the area under the intrauterine pressure curve in each ten-minute interval. The bar graph shows that infusing different doses of SNAP over 30-minute intervals in monkey depressed the uterine contractility index in a dose-dependent manner.

While even the lowest dose of 2.5 µg/kg/min of SNAP infusion was able to decrease contraction by about 30%, both 10 and 20 µg/kg/min doses were able to substantially decrease the contractility. Both 20 and 10 µg/kg/min doses of SNAP infusion for 30 minutes was able to decrease contraction during the infusion but also for another 30 minutes following the infusion.

Figure 4:
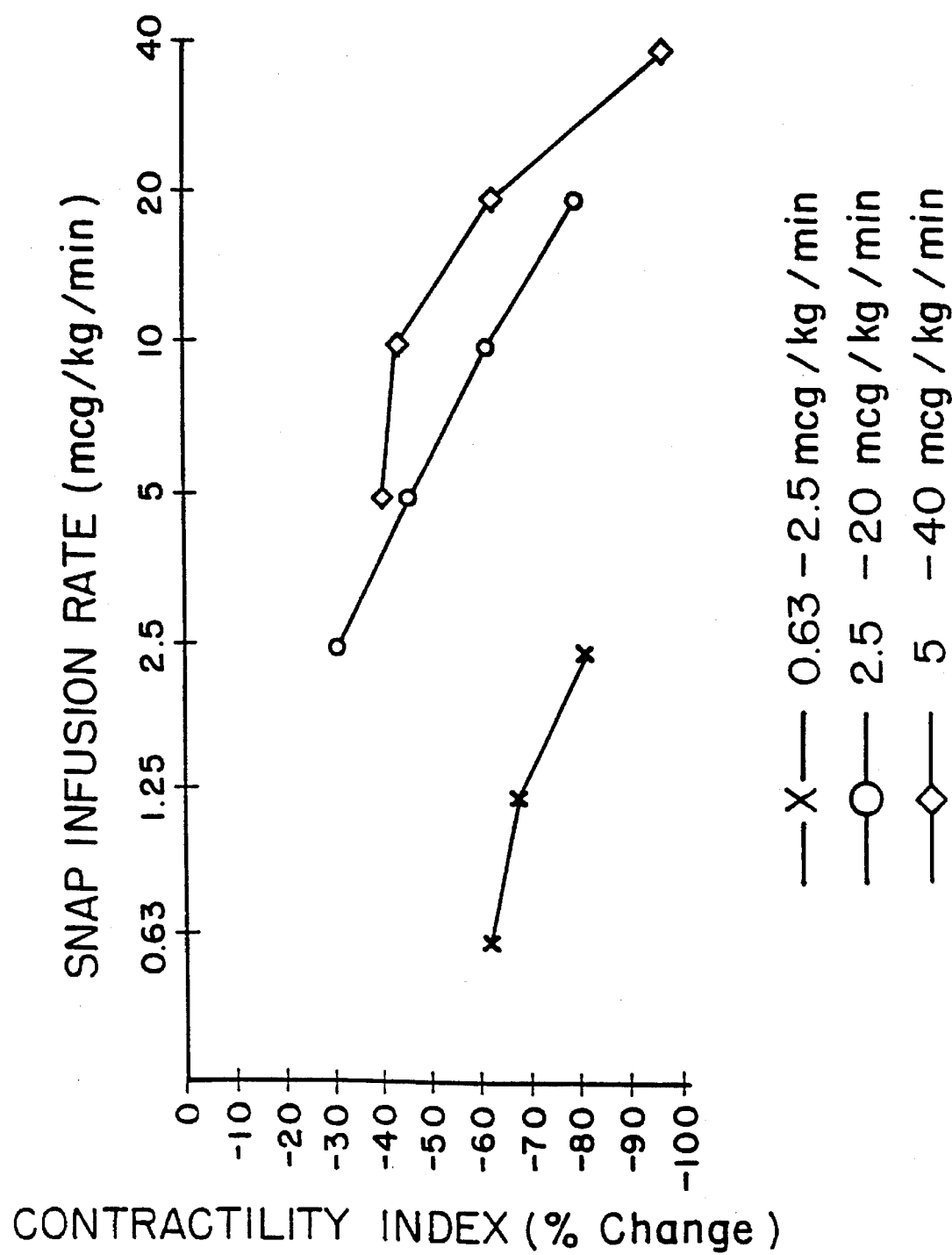
FIG. 4 depicts dose response curves expressed in % of change in contractility index observed in three rhesus monkeys.

FIG. 4 illustrates dose dependent response of the contractions in three monkeys. The curves were obtained by determination of % change of contractility index following the administration of various doses of SNAP. FIG. 4 illustrates dose response to administration of SNAP. As can be seen, the infusion rate from 0.63 to 2.5 µg/kg/min elicited the smallest response. The infusion rate from 2.5 to 20 µg/kg/ min elicited about 50% decrease in uterine contractility index while the infusion rate from 5–40 µg/kg/min elicited the greatest response. Each studied monkey had a different sensitivity to SNAP, probably reflecting the stage of preterm labor, but they all responded with a dose-dependent decrease in uterine activity.

The vasodilatory effect of SNAP infusion on preterm labor, that is the decrease in mean arterial pressure and increase in blood flow to the uterus were all dose dependent. There was no significant difference between SNAP infused into the systemic circulation via the femoral vein compared with similar doses infused directly into the uterine circulation via the hypogastric artery.

In vivo studies in monkey model confirmed that nitric oxide donor SNAP was able to suppress the virulent uterine contractions induced by surgical manipulation of the uterus. Infusion of SNAP suppressed and even ablated those contractions in dose dependent manner. These studies confirmed that SNAP-induced changes in uterine contractility and maternal hemodynamics were due to mediation through nitric oxide, since infusion of normal saline or N-acetyl-penicillamine (SNAP precursor) dissolved in dimethyl sulfoxide had no effect on the uterine contractility index or maternal hemodynamics.

The observation that exogenous nitric oxide inhibits post-operative preterm labor in the rhesus monkey in vivo provides new evidence of the mechanism of uterine smooth muscle contraction affected by the administration of nitric oxide source. Nitric oxide is known to relax vascular smooth muscle by activating guanylate cyclase and increasing cytosolic levels of guanosine 3':5'-cyclic monophosphate (cGMP). It would therefore be expected that compounds which increase cGMP levels would effect uterine contractility. In these monkey studies, nitroprusside increased cGMP levels but had no effect on spontaneous contractions. Attempts to provide cGMP directly by injecting 8-bromo-cGMP (5 mg/kg), a cGMP analogue, produced only transient reductions in uterine contractions in two monkeys. Attempts to raise levels of endogenous cGMP with Zaprinast, a cGMP-selective phosphodiesterase inhibitor described in Biochem. Pharmacol., 38:9–15 (1989) decreased the uterine contractility index by 35% in two monkeys. It is therefore clear that the nitric oxide activity on preterm labor contractions does not depend on whether the donor compound raises endogenous levels of cGMP or not.

Other nitrovasodilators, including nitroglycerin, hydroxylamine, and sodium azide, were also studied. Results were somehow surprising. Nitroglycerin 2 mg/kg/min infused into the chronic vested monkey, using model described in Example 1, had very little effect on either uterine contractility or maternal hemodynamics, suggesting the rhesus monkey lacks the specific tissue sulfhydryl groups necessary to form the S-nitrosothiol reactive intermediate that spontaneously releases nitric oxide. On the other hand, in sheep with spontaneous labor contractions and in human patients undergoing hysterotomy for fetal surgery, as seen in Example 7, it was observed that intravenous nitroglycerin given intraoperatively provided immediate relaxation of the contracted uterus and, given postoperatively, suppresses preterm labor. Thus, there seems to be a species difference in nitric oxide donors' effect on preterm labor contractions.

This finding confirms the utility of nitric oxide as effective tocolytic in humans. Human patients respond to SNAP and nitroglycerin while monkeys were shown to respond to SNAP and other nitric oxide donors but not to nitroglycerin.

One potential advantage of nitric oxide as a tocolytic is that it appears to increase blood flow to the uterus without at the same time effecting the fetus circulation. In current monkey studies, as expected, infusion of exogenous nitric oxide donor SNAP produced a dose-dependent vasodilation reflected in decreased maternal mean arterial pressure (MAP) and increased blood flow through the hypogastric artery to the uterus. The dramatic effect of exogenous nitric oxide in ablating uterine contractions suggests that endogenous nitric oxide may be responsible for maintaining uterine relaxation during pregnancy.

Effect of substrate for nitric oxide synthase, on preterm labor inhibition was also studied. Neither the administration of substrate, L-arginine to the contracting uterus, nor infusion of nitric oxide synthase inhibitors into the quiescent uterus were able to change the uterine contractility index. This suggested that nitric oxide availability in the intact pregnant monkey was not substrate dependent and sensitive. However, these compounds were observed to have an effect in human patients and in other species.

In vivo studies were further performed in sheep, using procedure of Example 5. Pregnant sheep were intravenously injected with nitroglycerin in doses from 1–3 µg/kg/min. These doses immediately abolished preterm contractions observed before. This further confirms that the effect of individual nitric oxide donors, substrates and NOS inhibitors is species dependent and cannot be predicted without extensive experimental determination of efficacy of each individual compound in each species, including humans.

In vivo studies performed in support of this invention determined that continuous production and availability of endogenous nitric oxide is responsible for uterine relaxation during pregnancy and that lack, decreased level or withdrawal of nitric oxide during pregnancy induces labor or parturition which is reversible upon administration of exogenous donor of nitric oxide in sufficient amount. Both the identity of the donor and the quantity of the exogenous nitric oxide donor are species dependent and must be individually determined.

Nitric oxide was conclusively shown to play a role in labor during pregnancy. Lack of nitric oxide results in preterm labor and can lead to premature delivery. The preterm labor is effectively countered by the method of current invention which provides to a pregnant woman or mammal suffering from preterm labor a sufficient amount of exogenous nitric oxide source compound able to inhibit preterm labor contractions and to allow continuation of normal pregnancy to term.

IV. In Vitro Studies

Current invention is further supported by studies done in in vitro conditions on rat pregnant uterus or mice myocytes. In these studies, nitric oxide synthase (NOS) activity was demonstrated in nerves, blood vessels and decidua of gravid rat uterus by the NADPH-diaphorase staining method and by other methods. NOS activity was quantitated in subcellular fractions of pregnant, laboring and post partum rat uterus. Results of these in vitro studies further confirm that NOS is present in multiple structures within the uterus. Its presence in two cellular compartments also suggests that more than one form of NOS is present in the uterus and that the uterine NOS is different from other known types of NOS.

Reduction in NOS activity at parturition shows that nitric oxide contributes to the maintenance of uterine contractile quiescence during gestation. Uterine tissue fixed during labor demonstrated markedly less NOS. Quantitation NOS activity in subcellular fractions of pregnant and laboring uterus revealed its presence in both the cytosolic and the membranous compartments of uterine homogenates. In both cellular subfractions the enzyme activity decreased significantly from pregnancy to term.

All these findings support the current invention which concerns a method for treatment, management, inhibition and control of preterm labor by administration of nitric oxide donor, or substrate in sufficient amount to exogenously supply endogenously missing or reduced nitric oxide.

For in vitro studies, isolated uterine tissue obtained from time-mated pregnant rats used according to procedure described in Example 2. Additionally, some studies were performed on mouse uterine myocytes.

1. Studies of Nitric Oxide Synthase

To determine whether nitric oxide donors can be converted to nitric oxide, levels of nitric oxide synthase were determined.

Nitric oxide synthase is the enzyme which converts nitric oxide substrate (L-arginine) to nitric oxide. The existence of up to six isoforms of the NOS enzyme are known from protein isolation studies. These forms differ primarily in their presence in either cytosolic or microsomal subfractions of tissues, their sensitivity to $Ca^{++}$/calmodulin, and by the inducement of their activity by a variety of factors and cytokines.

The presence of NOS in a tissue may be demonstrated histochemically with NADPH diaphorase reaction by its ability to reduce the nitro blue tetrazolium dye to a blueblack formazan. The reaction is NADPH-dependent. The diaphorase reduction has been demonstrated biochemically and immuno-histochemically using antibody to NOS which were previously shown to co-localizes with the formazan from NOS in the central and peripheral nervous system.

The present studies have demonstrated diaphorase staining in uterine nerves in the myometrium, endometrium, along uterine blood vessels and decidual endometrium. Such nerve staining was observed to be much more prominent in the pregnant than in the non-pregnant uterus.

Nitric Oxide Synthase Localization in Decidua, Vascular Endothelium, and Myometrial Nerve Plexus To determine whether uterus possess cellular mechanism for production of nitric oxide, the presence of NOS in decidua, vascular endothelium and myometrial nerve plexus was studied.

Full-thickness sections of virgin, pregnant, and postpartum rat and monkey uterus were stained via a modification of the NADPH-diaphorase staining method described in *Society of Neuroscience Abstracts*, 11:1201(1986).

Uterine samples were taken from 15–17 days gravid animals. Nitric oxide synthase (NOS) was localized within the intramural nerve fibers and the endothelium lining spiral arterioles within layers of the myometrium of the uterus.

The intensity and number of NOS positive nerve fibers was found to be greater in the gravid uterus than that in the virgin uterus and in the post-partum uterus. Staining of the gravid decidua produced the intense staining of the glandular epithelial cells whereas the glandular cells of the endometrium in non-pregnant uterus were only mildly stained. A post-term rat uterus where delivery occurred 12 hrs prior to sampling, showed only minimal staining of the decidual remnant and lesser staining of nerve fibers evidencing decreased NOS activity.

Characterization of NOS Enzyme in Rat Uterus

In order to determine the NOS function in pregnancy and preterm labor, its specificity with respect to its localization was studied by determining the co-factor requirements of the NOS enzyme in crude uterine subfractions.

The crude uterine subfractions were prepared by differential centrifugation. The NOS activity was determined using the $^3$H-arginine to $^3$H-citrulline conversion assay according to *Biochem. Biophys. Res. Comm.*, 185:960 (1992).

Two distinct types of NOS activity were found in the full-thickness of uterine tissue samples. A first activity was found to be present in a particulate, membrane bound fraction (30 kg pellet). This activity was not stimulated by calcium/calmodulin (specific activity ca 1.89 pmol/mg protein/min). The second activity was found in the soluble fraction (30 k xg supernatant) (specific activity ca 1.64 pmol/mg protein/min). This activity significantly increases in the presence of calcium and calmodulin (CaCal).

These results show that at least two different forms of the enzyme are present in uterus: a putative membranous form which is $Ca^{++}$-insensitive and a potentially cytosolic form which can be stimulated by $Ca^{++}$. These two enzymes seem to be different from the presently characterized NOS gene products which are known to be cytosolic $Ca^{++}$-sensitive (neuronal), cytosolic $Ca^{++}$ nonsensitive (macrophage), or a $CA^{++}$-sensitive membranous form (endothelial).

The particulate activity of the NOS found in uterus was shown to be different from the above three forms. These results suggest that novel, until now unknown forms of NOS are present in the uterus.

Comparison of NOS Activity in Pregnant, in Actively Laboring and in Post Partum Rat Uterus In order to confirm the function of NOS during pregnancy and its involvement in active labor, NOS activity in actively laboring rat uterus was compared to a post partum rat uterus.

The NOS activity was compared in subcellular fractions of the uterus of pregnant rats to that of the actively laboring rat uterus.

An increase in NOS activity was found during pregnancy when compared with the NOS activity during active labor and with post partum activity (FIG. 5A). This difference was significant in all subfractions of the enzyme (p=0.021–0.028). NOS enzyme activity was present in both crude soluble and membranous subfractions of uterine homogenates. The production of [$^3$H]-citrulline was linear with time for up to 60 minutes.

Figure 6:
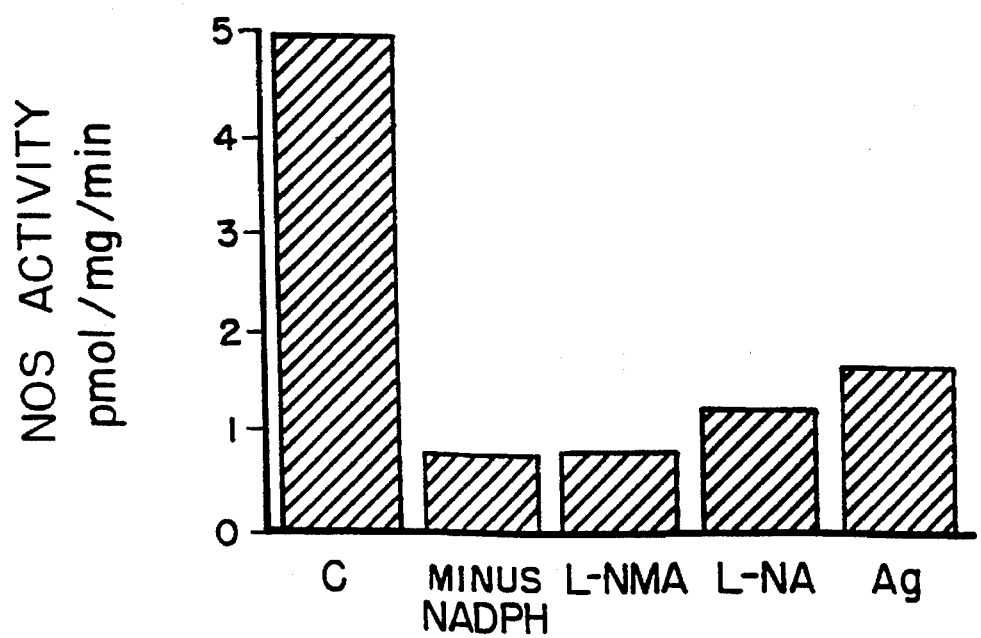
FIG. 6 depicts response of NOS activity to various NOS inhibitors.

When the NOS activity was inhibited with L-arginine analogs, enzyme activity seen in FIG. 6 in the presence of L-nitro-methylarginine (L-NMA) 0.5 mM was 20% of the total uninhibited NOS activity and in the presence of L-nitro arginine (L-NA) 0.5 mM, the NOS activity was 26% of total NOS activity. Aminoguanidine (AG) inhibited 34% of total NOS activity.

Ultracentrifugation of the post-mitochondrial supernatant fraction to resolve cytoplasmic and microsomal uterine subfractions verified that NOS activities measured in the more crude subfractions consisted of both cytoplasmic as well as microsomal membranous isoforms of NOS.

Figure 5:
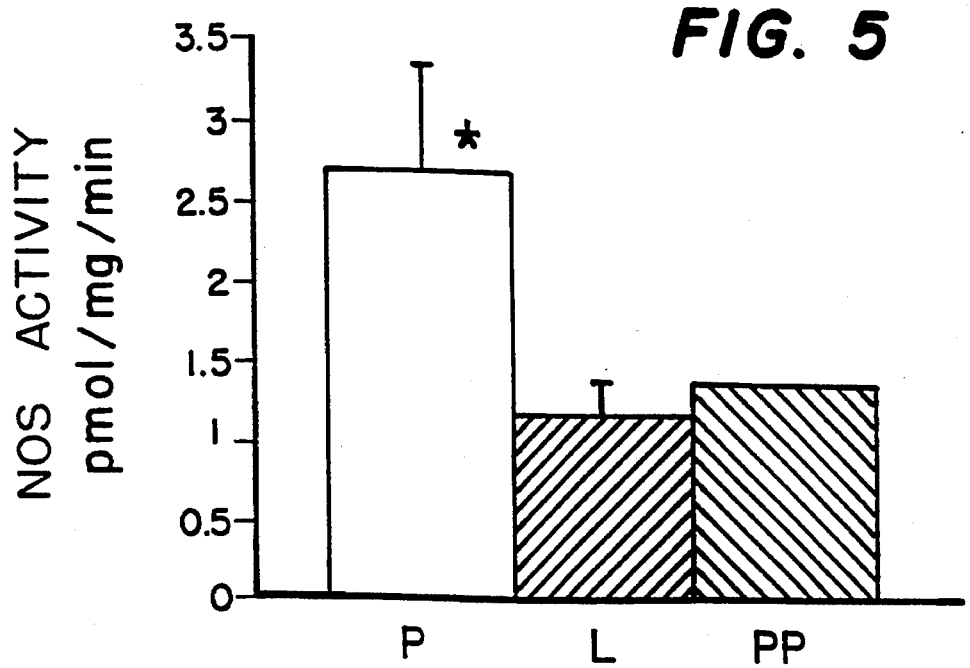
FIG. 5 depicts total nitric oxide synthase (NOS) activity in pregnant, laboring and post partum rat uterus.

Total NOS enzyme seen in FIG. 5 was highest at 2.7 pmols/mg/min ±0.68 in the preterm (P) 16 day pregnant uterus and declined significantly to 1.18 pmols/mg/min ±0.22 in term laboring tissue (L) or in post partum tissue (PP) to 1.4 pmols/mg/min ±0.13. In both subfractions, NOS activity could be increased by addition of calcium and calmodulin.

These data show that an increase in NOS function and in the endogenous production of nitric oxide during pregnancy is responsible for maintaining uterine quiescence and the retardation of labor.

Nitric Oxide Synthase Sensitivity to Calcium
During Labor

Sensitivity of NOS activity to calcium in cytosolic and membrane bound fraction during pregnancy was compared to that of during laboring. The method was according to Example 4.

Full thickness sections of rat uterus from 3 preterm gravid rats and 3 rats undergoing labor were stained by NADPH-diaphorase to localize NOS.

The activity of the NOS was determined by measuring the conversion of $^3$H-arginine to $^3$H-citrulline using crude cytosolic and particulate sub-fractions prepared from uteri removed from pregnant and laboring rats.

The production of $^3$H-citrulline was shown to be dependent on NADPH, and was shown to also be linear with time and protein concentration. Basal NOS activity (1 mM EGTA, no added calcium) was present in both, the soluble and the particulate cellular subfractions.

Histochemically, in the preterm gravid rat uterus sections, NOS was found to be localized within the myometrial neuronal varicosities, in the fine nerves surrounding blood vessels, in the vascular endothelium and in the entire decidua. The laboring rat uterus sections showed only minimal NOS staining in the decidual remnant and in the neural plexi within the myometrium.

NOS activity and its dependency or calcium and calmodulin was different in the cytosolic and membrane fractions as well as in the pregnant and laboring uterine samples. Results are shown in FIG. 7.

Figure 7A:
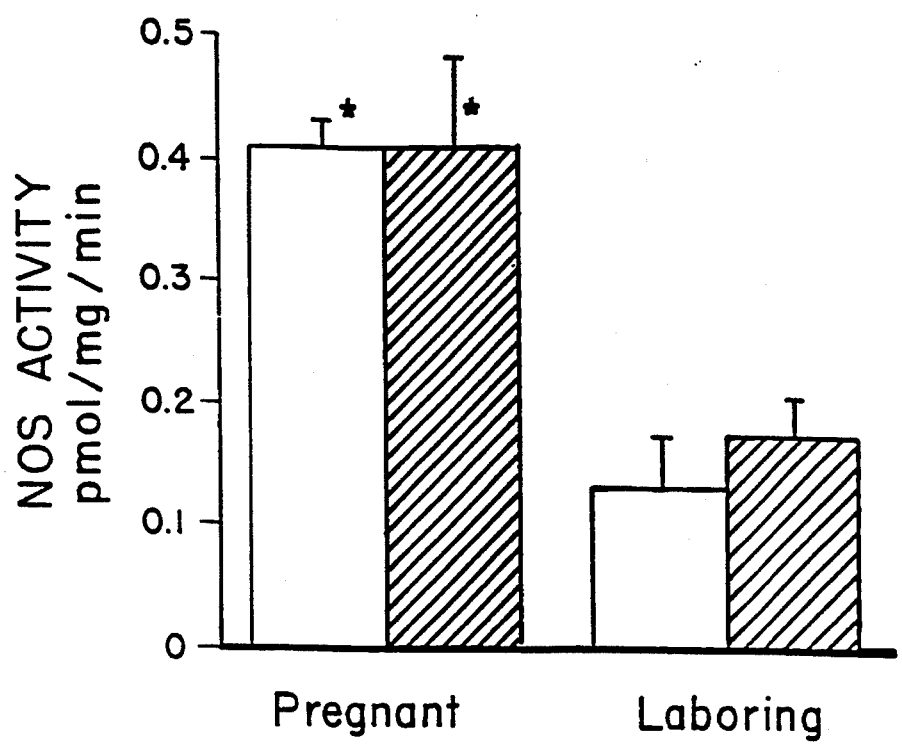
FIGS. 7A and 7B depict NOS activity found in cytosol in pregnant or laboring rat uterus FIG. 7(A), and in membrane bound NOS in pregnant and laboring rat uterus FIG. 7(B).

FIG. 7A illustrates NOS activity found in the cytosol. NOS activity (N=5) in the cytosolic subfraction was measured independently of calcium and calmodulin (–CaCM in white). Activity decreased significantly (p<0.05) from pregnancy to labor. NOS activity measured in the presence of 3 mM calcium and 50 U calmodulin (+CaCM in gray) represents additional activity that is dependent on the presence of calcium. The decrease from pregnancy to labor in this group was also significant where p<0.05.

In both these groups of uterine NOS activity found in cytosol, the activity of NOS found in laboring uterus was significantly, about 63%, lower than in the pregnant uterus.

Figure 7B:
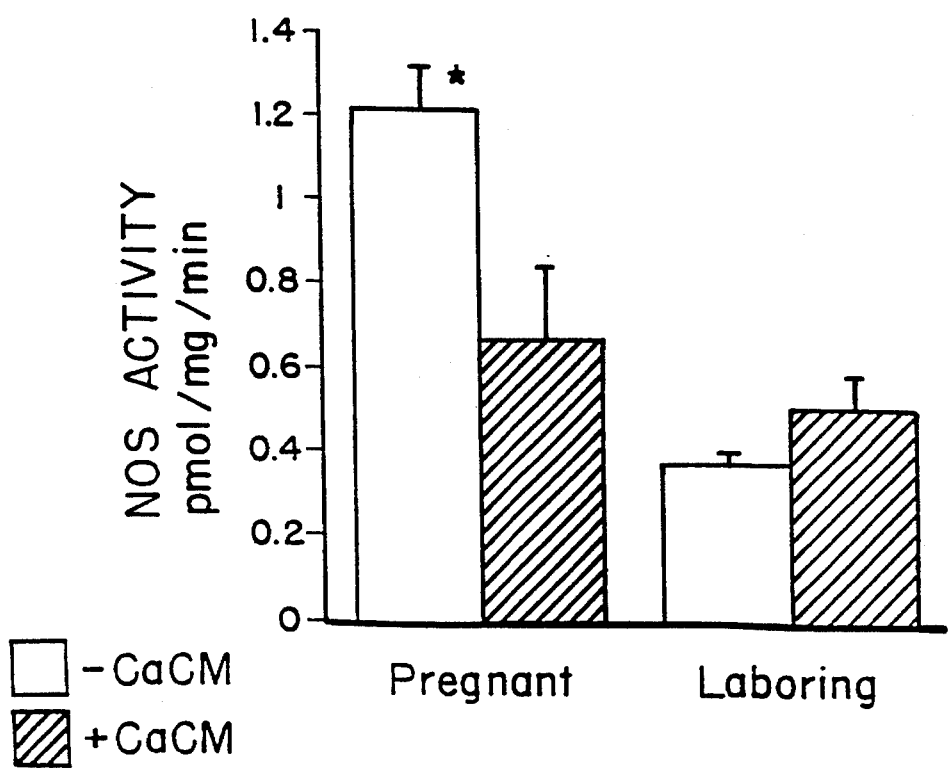

FIG. 7B illustrates NOS activity found to be membrane bound. NOS activity (N=5) in the particulate subfraction was measured in the absence (–CaCM in white) and presence of (+CaCM in gray) 3 mM calcium and 50 U calmodulin. The decrease in NOS activity in the –CaCM group was significant (p<0.05), while NOS activity that was dependent upon the presence of calcium and calmodulin did not change significantly from pregnant to laboring tissue.

The greatest portion of the total enzyme activity was measured in the membrane bound subfraction. The total calcium insensitive NOS activity in pregnant uterus was around 1.2 pmoles/mg/min., while the total calcium sensitive activity was around 0.7 pmoles/mg/min. In laboring uterus, the activity of calcium insensitive NOS decreased to about 0.4 pmoles/mg/min., that is by about 68%, while the activity of calcium sensitive NOS decreased only slightly to about 0.5 pmoles/mg/min., that is by only about 25%, as seen in Table 2.

The addition of calcium and calmodulin increased NOS activity. The presence of two enzymes, a calcium-sensitive and a calcium-insensitive form of the NOS enzyme in both uterine subfractions was indicated. In uteri of laboring rats, the basal and the calcium-stimulated activities of both the NOS enzymes were significantly reduced. Despite the fact that the overall activity of NOS was reduced in laboring uteri, the higher activity of the calcium augmented versus the basal activity of NOS in laboring uteri indicated a differential reduction in the calcium-insensitive isoforms(s) of the NOS enzyme. The results obtained are shown in Table 2 below.

TABLE 2

Decrease in NOS Activity from Pregnancy to Labor

| location | calcium dependence | % decrease in activity |
|---|---|---|
| cytosol | – | 68%* |
| cytosol | + | 59%* |
| membrane | – | 69%* |
| membrane | + | 25% |

*p < 0.05 by one way ANOVA.

The activity of both the calcium sensitive and insensitive forms of the NOS enzyme are present in the gravid rat uterus and these activities are reduced in laboring uteri. These changes in the activities of the NOS enzymes are consistent with a nitric oxide role in the maintenance of uterine quiescence during gestation.

The presence of NOS in the different uterine structures suggests the presence of multiple molecular forms of NOS in the uterus. NOS isoforms are defined by their molecular weight, location within the cytosolic or membrane bound compartments of the cell, sensitivity to stimulation by calcium and calmodulin, and constitutive verses inducible regulation of enzyme activity. The enzyme characterization data suggests there may be as many as four NOS isoforms from pregnancy to parturition which may facilitate labor. Inhibition of NOS activity by the arginine analogs, L-NMA and L-NA, and aminoguanidine, as seen in FIG. 6, confirms that the measured activity is NOS. The NOS activities that underwent the greatest decline between the quiescent and laboring state of pregnancy were the calcium-independent activities present in the cytosol and membrane particulate subfractions.

In Vitro SNAP Inhibition of Contractions in
Pregnant Rat Uterine Muscle Tissue

To determine the effect of nitric oxide donors on contractions of pregnant rat uterus, the effect of the nitric oxide donor SNAP on the occurrence of spontaneous contractions was tested using isolated pregnant rat uterine muscle strips suspended in tissue baths containing an oxygenated Krebs solution.

Uterine muscle strips from virgin and 18–19 day pregnant Fischer rats were isolated and mounted in jacketed tissue baths and connected to isometric force transducers. The changes in tension versus time were displayed on a computer-generated polygraph. The muscle strips were maintained in standard oxygenated Krebs solution at 37° C. The mechanical responses to L-arginine, D-arginine, nitric oxide donors nitroglycerin, sodium nitroprusside, DEA NO, DETA/NO and spermine and nitric oxide synthase inhibitors N-nitro-L-arginine (L-NA), and N-nitro-L-arginine methyl ester (L-NAME) were measured after spontaneous or agonist-induced contractions. Dose response curves were created and analyzed.

Nitroglycerin relaxed the uterine strips in a dose dependent manner. Diethylamino nitric oxide (DEA-NO) which liberates nitric oxide spontaneously relaxed uterine tissue significantly. Sodium nitroprusside, however, had no effect on uterine tone. In the virgin (n=2) and one group of gravid rats (n=4) uterine contractility was not significantly affected by inhibition of nitric oxide synthase with L-NA or L-NAME. L-arginine added to the tissue bath caused a significant decrease in spontaneous and oxytocin-induced uterine contraction that lasted approximately 5 minutes. D-arginine produced the same results.

Nitric oxide via nitric oxide donors causes relaxation of uterine smooth muscle when provided exogenously. Sodium nitroprusside is a potent nitroprusside which requires bio-activation. Rat uterine tissue may be lacking the mechanism of activation. The results suggest that endogenous uterine nitric oxide exists.

Induction of Nitric Oxide Synthase Activity in Primary Mouse Uterine Myocytes To determine whether the myometrium was a site of nitric oxide synthesis, nitric oxide synthase activity induction was studied in primary mouse uterine myocytes.

Primary myocytes were prepared from scraped uteri of pregnant mice at day 14 of gestation. NOS activity was measured using the conversion of $^3$H-arginine to $^3$H-citrulline. At this point in gestation, about 70% NOS activity was present in the myocytes. NOS inhibitor L-NAME (1 mM) inhibited NOS activity of control myocytes. The $Ca^{2+}$ ionophore A23187 (1 μM, 10 min.) failed to further stimulate myocyte NOS activity. This result indicates that myocyte NOS might be different from calcium dependent constitutive neuronal and endothelial NOS isoforms, and suggested properties similar to inducible forms of NOS.

The ability of cytokines to induce myocyte NOS activity was also evaluated. The cytokines studied were TGF-β1 and CSF-1, chosen because concentration of both have been shown to increase within the uterus throughout pregnancy. LPS and γ-IF, IL-1 and TNF-α were also tested to compare uterine myocyte NOS response to known inducers of macrophage and vascular smooth muscle NOS.

Incubation of the cell cultures for 24 hours with LPS (10 μg/ml)/γ-IF (100 U/ml), IL-1β (20 ng/ml)/TNF-α (100 ng/ml), CSF (100 ng/ml), or TGF-β1 (20 ng/ml) caused no significant change in NOS activity. However, treatment with CSF-1 in the presence of TGF-β1 caused a significant increase in NOS activity (5.1±1.1 fold of basal, p<0.01 by one-way ANOVA, Scheffe post hoc test, n=6). TGF-β1 dose responses were linear in the range of 0.2–20 ng/ml. Inhibition of Eicosanoid synthesis by the addition of $10^{-5}$ meclofenamate to culture media shifted the dose response curve for TGF-β1 to the left. CSF/TGF induction was inhibited by L-NAME (1 mM), dexamethasone ($10^{-5}$ M) and $PGE_2$ ($10^{-4}$ M).

These in vitro experiments show that smooth muscle cells isolated from the gravid mouse uterus express a form of NOS activity which is inducible by CSF-1 and TGF-β1 in combination, and is inhibited by the presence of prostaglandins in particular $PGE_2$. This cytokine response differs from the classic induction response seen in macrophage or vascular smooth muscle NOS, further confirming the presence of a unique form of NOS regulation in the uterus which would be a critical component of any uterine-specific mechanism for the autoregulation of myometrial contractility by nitric oxide.

Characterization of Nitric Oxide Role in Normal Pregnancy and Preterm Labor

Nitric oxide synthase is localized in myometrium, decidua, placenta, and uterine nerves. Changes in these areas in rat uterus were documented during pregnancy and delivery using histochemical staining as described above. NOS enzyme function was additionally assayed in non-gravid, gravid, and postpartum uterus.

Virgin, pregnant, and post-partum monkey uterus were used for nitric oxide synthase localization using diaphorase staining and arginine to citrulline enzyme assay as described in previously. In these samples, diaphorase staining was strikingly increased by pregnancy and NOS activity appeared to be concentrated in the branching neural network within the myometrium as well as in the decidua. Similarly to rat uterus, NOS activity changes were observed in monkey uterus in a progression from the non-pregnant to the pregnant and then the post-partum state. Uterine muscle strips consisting of full thickness (including decidua) or myometrium only were used to determine the layer of the uterus most responsible for nitric oxide mediated relaxation.

Studies of monkey uterus NOS activity and increase during pregnancy described above showed a strikingly higher diaphorase staining in gravid over non-gravid monkey uterus.

The all above discussed results of in vitro studies support the current invention and confirm results of in vivo studies which show that nitric oxide is directly involved in maintaining uterus relaxation during pregnancy. When the endogenous levels or availability of nitric oxide decrease, the uterus respond with increased contractility resulting in labor. When this occurs prior to normal term of pregnancy, such decreased level of nitric oxide results in preterm labor. By providing exogenous nitric oxide source or donor, the preterm contractions can be inhibited and the preterm labor stopped before resulting in preterm delivery.

V. Clinical Studies

Treatment of preterm labor with known tocolytic agents, especially the virulent labor induced by hysterotomy for fetal surgery, has proven largely ineffective. Moreover, such treatment presents definite danger for both mother and the fetus because the somehow effective vasodilating concentrations of known tocolytics are too high and cause definite toxic reactions. After demonstrating in rhesus monkeys and in sheep that nitric oxide, a potent smooth muscle relaxant, ablated labor even after hysterotomy, nitroglycerin was tested during and after hysterotomy for fetal surgery in eight patients.

In an attempt to control strong hysterotomy induced contractions, it was surprisingly found that intraoperative uterine contractions responded to intravenous nitroglycerin given as a single injection or as a continuous infusion in three patients and nitroglycerin infusion was therefore used as the primary tocolytic in other patients undergoing hysterotomy and fetal thoracotomy. In contrast to all previous tocolytic regimens attempted in this setting, nitroglycerin infusion produced profound uterine relaxation and ablated postoperative preterm labor without apparent ill effect on mother or fetus.

Typically, uterine relaxation requires a depth of anesthesia which is known to produce myocardial depression in both mother and fetus. Regimen of postoperative tocolysis using magnesium sulfate and betamimetics as well as indocin proved inadequate because doses required to suppress uterine activity proved toxic for mother and dangerous for the fetus. Specifically, maternal volume restriction thought necessary to avoid pulmonary edema when using high-dose magnesium sulfate and terbutaline produces uteroplacental hypoperfusion, and indocin can produce right-heart failure manifested in patients by tricuspid regurgitation.

Based on experimental work in in vivo monkeys and sheep and in vitro rat uterus and on the initial clinical experience over the past decade, a regimen was developed in which a nitric oxide donor, such as nitroglycerin infusion was used as primary tocolytic agent during and after fetal surgery. The regimen is described in Example 6.

The effect of nitroglycerin on the preterm uterine contractions after uterine manipulation was originally studied in patients undergoing fetal surgery.

Following the hysterotomy, patients experienced several episodes of visible and palpable uterine contractions. In three patients, these contractions were treated with single intravenous doses of 50–100 µg nitroglycerin intravenously. Within 5–10 seconds the contracted uterus completely relaxed and the labor stopped. In the next two patients, the contractions were treated with an infusion of nitroglycerin. Response to demonstrated episodes of uterine contraction to nitroglycerin infusion resulted in ablation of contractions which persisted while the infusion continued.

The method of the current invention utilizes for the first time a nitric oxide donor drug for tocolytic management of preterm labor. Based on the hypothesis that nitric oxide was shown to be an important mediator of uterine smooth muscle relaxation, the ability of nitric oxide donor drugs to ablate preterm labor in the rhesus monkey and in laboring sheep, it has been now demonstrated that nitroglycerin ablates labor after hysterotomy in fetal surgery. The discovery that otherwise commonly used class of drugs has also a powerful tocolytic effect allows management of prevalent and devastating problem of spontaneous preterm labor. The potential for treating spontaneous or surgically induced preterm labor is particularly appealing because nitroglycerin and other nitric oxide donor drugs can be used effectively by a variety of routes including infusions, transcutaneous patches and sublingual depositories making chronic outpatient treatment relatively simple.

The discovery also eliminated original concerns about toxicity of nitroglycerin in pregnant women. In the studies supporting the invention, nitroglycerin infusion provided profound uterine relaxation during and after fetal surgery and appeared well tolerated by both mother and fetus. Use of nitroglycerin for tocolysis allowed reduced levels of inhalation anesthesia intraoperatively and modified the need for volume restriction and hemodynamically destabilizing drugs postoperatively. Nitroglycerin infusion does, however, require continuous monitoring of mean arterial pressure and central venous pressure in an intensive care setting.

One major concern during development of this invention was that nitroglycerin infusion might have an ill-effect on the fetus. Although nitroglycerin and other nitric oxide donor drugs have been well-studied in the treatment of myocardial infarction, heart failure, and other clinical settings, they have not been extensively studied during pregnancy. While the effect on maternal hemodynamics is well-understood and predictable, possible hemodynamic adverse effects on uteroplacental perfusion and fetal hemodynamics were unknown. Exogenous nitric oxide was shown to increase uterine artery flow in monkey even though mean arterial pressure was decreased. But the major concern with nitroglycerin was that drug that crosses the placenta could dilate the normally constricted fetal vascular beds particularly the pulmonary vascular bed. Indeed, nitric oxide donor drugs given directly to the fetus do produce vasodilation and change blood flow distribution in fetal lambs. However, in acute studies in both sheep and monkeys these symptoms have thus far not been observed. No significant hemodynamic change or metabolic consequence for the fetus from infusion of high doses of nitroglycerin and other nitric oxide donor drugs was detected. Nitroglycerin was rapidly metabolized in the maternal circulation and its transplacental passage appeared to be poor, at least in the sheep, where it has been measured. Individual patient's case reports are described in Example 7.

It has now been shown that exogenous nitric oxide ablates preterm labor in monkeys and sheep and it was also demonstrated that nitroglycerin infusion produces profound uterine relaxation after hysterotomy for fetal surgery in humans. The effectiveness of exogenously administered nitric oxide sources in preterm labor confirms that endogenous nitric oxide production in the myometrium allows uterine relaxation to accommodate pregnancy and that withdrawal of nitric oxide-mediated uterine relaxation produces labor at parturition and that the pharmacologic manipulation of nitric oxide may provide the first effective treatment of preterm labor. Experimental work in rats, sheep and monkeys is consistent with these findings.

VI. Pharmaceutical Compositions

One of the compositions of the invention finds an application in the retardation or inhibition of uterine contractions to prevent or retard labor, particularly preterm labor. Another composition of this invention finds an application in the induction or augmentation of uterine contractions to promote labor such as in the induction of parturition at maturity, and in the promotion of early termination of pregnancy.

a. Compositions for use in Method I

This invention provides compositions suitable for control, inhibition and management of preterm labor.

The composition typically comprises a uterine relaxant selected from the group consisting of agents capable of potentiating the effect, or increasing the level, of nitric oxide in utero, such as nitric oxide donors, substrates, precursors and sources, and mixtures thereof.

Optionally, a second agent selected from the group consisting of other tocolytic agents, analgesics, vasopressors, and mixtures thereof are added to the nitric oxide source.

Nitric oxide source suitable for use in the composition of this invention that are capable of potentiating the effect, or increasing the level of nitric oxide in utero include S-nitroso-N-acetylpenicillamine (SNAP) and analogues thereof, nitric oxide nucleophiles or nitric oxide adducts such as diethylamino/nitric oxide, DETA/NO, spermine or other nucleophilic groups known in the art, nitroglycerin and analogues thereof such as isosorbide dinitrate, nitropaste, nitropatches, nitroprusside and analogues thereof, other nitrovasodilators such as hydroxylamine, sodium azide, 2-isosorbide mononitrate, PETN, and analogues thereof and endogenous precursors of nitric oxide such as L-arginine.

The nitric oxide source described above may be present in the composition in an amount of about 0.01 to 99 wt %, preferably in an amount of about 0.1 to 85 wt %, and still more preferably about 1 to 20 wt %. However, other amounts of the nitric oxide source are also suitable.

Specific agents may be present in the following amounts. SNAP and similarly acting compounds may be present in the composition in an amount of about 0.1 to 15 wt %, preferably about 0.5 to 10 wt %, and more preferably about 1 to 8 wt %. Nucleophile/nitric oxide adducts such as DEA/nitric oxide and similarly acting mixtures may be present in the composition in an amount of about 0.01 to 18 wt %, preferably about 0.1 to 15 wt %, and more preferably about 1 to 10 wt %. Nitroprusside and similarly acting agents may be present in the composition in an amount of about 0.01 to 10 wt %, preferably about 0.1 to 8 wt %, and more preferably about 1 to 5 wt %. Nitroglycerin and similar acting agents may be present in the composition in an amount of about 0.01 to 20 wt %, preferably about 0.5 to 10 wt %, and more preferably about 0.8 to 8 wt %. However, other amounts of these compounds are also suitable as long as they are not toxic to the mother or to the fetus.

Other tocolytic agents suitable for use in the labor retarding composition as the second agent include β-adrenergic agonists, oxytocin antagonists, prostaglandin synthesis inhibitors such as prostaglandin synthetase inhibitors, magnesium salts, calcium transport blockers, ethanol, phosphodiesterase inhibitors, and progestins, among others.

Typically, the other tocolytic agents may be present in the composition in an amount of about 0.01 to 90 wt %, and more preferably about 1 to 25 wt %. However, other amounts may also be utilized.

Among the tocolytic agents, preferred amounts for specific compounds are described below.

Within the context of this patent, a β-adrenergic agonist is defined as any compound or mixture of compounds capable of stimulating one or more types of β-adrenergic receptors. The β-adrenergic agonists may be present in the composition in an amount of about 0.01 to 10 wt %, and more preferably about 1 to 5 wt %, although other amounts are also suitable. β-adrenergic agonists suitable as tocolytic agents include epinephrin, isoproterenol isopropylnorepinephrine), p-hydroxyphenylisopropylarterenol), isoxsuprine, orciprenaline, (1-(3,5-dihydroxyphenyl)-2-isopropylaminoethanol sulfate, salbutamol, terbutaline, analogues thereof, and other agents known in the art.

A prostaglandin synthesis inhibitor is defined as a compound or mixture of compounds which inhibit any step or steps in the series of enzymatic reactions involved in the synthesis of prostaglandins. Prostaglandin synthesis inhibitors suitable for use as tocolytic agents include indomethacin(1-(p-chlorobenzoyl)-5-methoxy-2-methylindole-3-acetic acid), naproxen, aspirin, meclofenamic acid, phenylbutazone, analogues thereof, and other agents. The prostaglandin synthesis inhibitors may be present in the composition in an amount of about 0.01 to 90 wt %, and more preferably about 1 to 10 wt %. However, other amounts are also suitable.

Magnesium salts suitable as tocolytic agents include $MgSO_4$ and other inorganic and organic salts. The magnesium salts may be present in the composition in an amount of about 0.5 to 10 wt %, and more preferably about 5 to 20 wt %. However, other amounts are also suitable.

Within the context of this invention, a calcium transport blocker, a term herein used interchangeably with calcium channel-blocking agent, is defined as any compound or mixture of compounds capable of reducing importation of extracellular calcium. Calcium transport blockers suitable for use herein as tocolytic agents include nicardipine, nitrendipine, nifedipine, analogues thereof, and other agents known in the art. The calcium transport blockers may be present in the labor retarding composition in an amount of about 0.5 to 15 wt %, and more preferably about 1 to 20 wt %. Other amounts are, however, also suitable.

The progestins provided for use as tocolytic agents include progesterone, pregnanolone, pregnanedione, epipregnanolone, allopregnanolone, allopregnanedione, analogues thereof, and other agents known in the art. The progestins may be present in the composition in an amount of about 0.5 to 30 wt %, and more preferably 1 to 15 wt %. However, other amounts are suitable. The ethanol may be present in an amount of about 1 to 20 wt %, and more preferably about 5 to 15 wt %. However, other amounts are also suitable.

The phosphodiesterase inhibitors provided by the invention as suitable tocolytic agents include papaverine, aminophylline, cilostamide, valeramide, zaprinast, rolipram, amrinone, dipyridamole, theophylline, analogues thereof, and other agents known in the art. These inhibitors may be present in the composition in an amount of about 0.5 to 18 wt %, and more preferably about 1 to 10 wt %.

Other tocolytic agents, such as oxytocin antagonists, may be present in suitable amounts as known in the art, or in lower amounts taking into consideration the presence of the uterine relaxant agent in the composition.

The present composition may also include other agents typically used for administration to a preterm labor patient. Some of these agents such as, for instance, those intended for countering the side effects of the components of the composition, are listed below. However, other agents may also be incorporated in amounts that are known to the practitioner.

Analgesics for use in conjunction with the present nitric oxide source include acetaminophen, acetylsalicylic acid, morphine, fentanyl, or other similar acting agents known in the art, and mixtures thereof. The analgesics may be present in the composition of the invention in an amount of about 0.1 to 18 wt %, and more preferably about 5 to 20 wt %. However, other amounts are also suitable.

Vasopressors may be used in conjunction with the nitric oxide source to counter the vasodilating effect of the latter. Suitable vasopressors include α-adrenergic agonists such as ephedrine, norepinephrine, dopamine and epinephrine, analogues thereof, and other similar acting agents known in the art. The vasopressors may be present in the composition of the invention in an amount of about 0.01 to 10 wt %, and more preferably about 1 to 5 wt %. However, other amounts are also suitable as is known in the art.

The labor retarding composition may further comprise a pharmaceutically acceptable carrier. The pharmaceutically acceptable carrier may be polycarbophil, sucralfate, carboxymethylcellulose, β-cyclodextrin or other compounds known in the art. Other carriers known in the art that are pharmaceutically acceptable are also within the scope of this invention.

The following are preferred embodiments of the labor retarding composition.

In one preferred embodiment, the labor retarding composition comprises a uterine relaxant capable of potentiating the effect, or increasing the level, of nitric oxide in utero.

In another preferred embodiment of this invention, the labor retarding composition comprises a uterine relaxant selected from the group consisting of SNAP, nucleophile/nitric oxide adducts, nitroprusside, nitroglycerin, analogues thereof, and mixtures thereof.

In a more preferred embodiment, the composition comprises nitroglycerine, analogues thereof or mixtures thereof.

Further preferred is a labor retarding composition comprising SNAP, analogues thereof, or mixtures thereof.

Also preferred is a labor retarding composition comprising nucleophile/nitric oxide adducts such as DEA/nitric oxide, analogues thereof, or mixtures thereof.

Additionally preferred is a labor retarding composition comprising a uterine relaxant selected from the group consisting of nitroprusside, analogues thereof, and mixtures thereof.

In one particularly preferred embodiment of the invention, the labor retarding composition comprises a uterine relaxant selected from the group consisting of SNAP, DEA/nitric oxide, nitroprusside, nitroglycerin, analogues thereof, and mixtures thereof, and a phosphodiesterase inhibitor, and papaverine.

An additional preferred embodiment of the invention is a labor retarding composition comprising L-arginine, metabolic precursors thereof, analogues thereof, or mixtures thereof, along with a phosphodiesterase inhibitor such as papaverine or zaprinast.

b. Compositions for use in Method II

Also provided herein are labor promoting compositions to be used in a method for promoting uterine contractions that comprises administering to a pregnant subject in need of such treatment a uterine contracting agent capable of countering the effect, or reducing the level of nitric oxide in utero, in an amount effective to promote uterine contractions of a desired intensity and to maintain the contractions for a desired period of time, and optionally induce parturition.

Uterine contracting agents suitable for use in this variation of the invention are capable of potentiating the effect, or decreasing the level, of nitric oxide in utero include nitric oxide synthetase inhibitors such as $N^{\omega}$-nitro-L-arginine (L-NA) and analogues thereof, and $N^{\omega}$-methylarginine (NMA) and analogues thereof, $N^{\omega}$-monomethyl arginine (L-NMMA), $N^{\omega}$-nitro-L-arginine methyl ester (L-NAME), and other similar acting agents, and mixtures thereof.

The uterine contracting agents discussed above may be present in the composition in an amount of about 0.01 to 99 wt %, and more preferably about 0.1 to 85 wt %. However, other amounts of uterine contracting agents may also be used. Amounts which are suitable for specific uterine contracting agents of the invention are set forth below.

Within the context of this invention, a nitric oxide synthetase inhibitor is defined as any compound or combination of compounds capable of inhibiting the nitric oxide synthetase catalyzed conversion of L-arginine to nitric oxide and citrulline.

LNA and similar acting compounds may be present in the composition in an amount of about 0.2 to 23 wt %, and preferably about 1 to 12 wt %. NMA and similar acting compounds may be present in the composition in an amount of about 0.2 to 23 wt %, and more preferably about 1.5 to 15 wt %. Methylene blue, and its analogues and similar acting compounds may be present in the composition in an amount of about 1 to 25 wt %, and more preferably about 1.5 to 12 wt %. N-methyl arginine and similar acting compounds may be present in the composition in an amount of about 0.2 to 23 wt %, and more preferably about 1.5 to 15 wt %. Nitroarginine methyl ester and similar acting compounds may be present in the composition in an amount of about 0.2 to 60 wt %, and more preferably about 3 to 30 wt %. Other amounts, however, are also suitable.

Any compound that reduces the level of nitric oxide is suitable as the uterine contracting agent for use in this composition. Examples of these are described above, as are the amounts in which they may be present in the compositions of this invention.

The present composition may also include other agents that are typically used for administration to a pregnant patient in need of labor induction and/or augmentation or to counter the side effects of the ingredients present therein. Some of these are listed below. However, other agents may also be incorporated.

Suitable uterine contracting agents that are capable of reducing the levels of nitric oxide, in utero were described above. The uterine contracting agents suitable for use with this invention may be administered to the pregnant subject in an amount of about 1 to 500 mg/kg/day, and more preferably about 2 to 250 mg/kg/day. However, other amounts may also be utilized as determined by a practitioner.

VII. Administration

The method of the invention may be practiced by means of a single administration, or if needed, by infusion over a period of time, as considered appropriate by a practitioner. Thus, a single administration or multiple administrations, e.g., daily or at other intervals, as indicated by the practitioner, may be used.

The composition in accordance with this method may be administered orally, transdermally, subcutaneously, intravenously, intraperitoneally, intramuscularly, intranasally, rectally or intravaginally.

The composition may be in the form of a tablet, capsule, oral, liquid, implant, injectable preparation, suppository, ointment, cream, patch, sponge, suspension, emulsion, or other formulation suitable for iontophoresis. The composition of the invention may be prepared by powdering the various desired compounds, and optionally the carrier as is known in the art. In the use of a liquid delivery system, the compounds may be dissolved in a liquid carrier and the like. In the case of a cream or an ointment, the various carriers are blended with the compounds so that they are suspended or dissolved therein.

The present composition may be administered to a pregnant subject alone or, be it a human or non-human mammalian subject, in conjunction with other therapies known in the art.

The method of the invention may be practiced by means of a single administration, or is needed, by infusion over a period of time as considered appropriate by a practitioner. Thus, a single administration or multiple administrations, e.g., daily or at other intervals or by infusion, as indicated by regimen developed by the practitioner, may be used. Typically, when the onset of preterm labor is noticed by one of many detection means, the practitioner may administer an initial dose of the composition of the invention as described above.

Upon further monitoring, a decision may be made as to whether further intervention is necessary or a single administration has countered the initiation of labor. If after a certain period of time, the contractions reappear, a further administration of the composition may be undertaken. The present composition may be administered for a period of time of about 1 minute to 9 months continuously in nontoxic amounts. The time for which the administration is undertaken depends on the time needed to prolong pregnancy to a number of weeks into the term that will make the fetus viable.

The nitric oxide sources may be administered in amounts, doses and intervals within the range described above. However, each individual nitric oxide source may be administered in particularly preferred ranges of dosages.

The application of the method of the invention may be discontinued when the patient reaches a point during the pregnancy term that permits parturition and the delivery of a healthy newborn.

UTILITY

The method of the present invention may be applied to subjects such as human and non-human mammalian females. Preferred use is the treatment of pregnant woman experiencing preterm labor or experiencing overterm pregnancy. Examples of non-human mammalian animals are primates, equines, bovines, ovines, porcines, canines, felines, and rodents. Examples of other animals that may benefit from the present treatment are all types of animals held in captivity such as zoo animals and pets such as canines and felines, among others. The field of animal husbandry provides a broad application for the present method.

The contractile quiescence of the uterus is essential for implantation of the fertilized ovum and for maintenance of pregnancy. Despite numerous studies attempting to understand the changes that initiate parturition at term, little had been known up to the present time on how labor is triggered at term, or how preterm labor arises. A conceptual obstacle has been the lack of agreement as to whether labor is the result of a new process initiated at term or the termination of a process maintained throughout gestation. The latter concept is favored primarily because it is more consistent with the observation that the pregnant uterus remains quite refractory to a variety of stimuli. This suggests an active inhibition of contractions, which normally subsides at term. While the endogenous process by which term labor is initiated remains obscure, a more pressing clinical issue is the etiology of preterm labor. Preterm labor represents a disruption of the uterine quiescence that characterizes normal gestation. It is widely known that as a consequence of early parturition, preterm labor usually increases the rate of morbidity and mortality in neonates.

Administration to a pregnant of a female compounds that increase the level of any of nitric oxide in utero results in uterine relaxation. This invention, therefore, provides the use of pharmacological agents capable of increasing the level of these nitric oxide sources in utero as an effective treatment for preterm labor.

EXAMPLE 1

A Non-Human Primate model for Study of Preterm Labor

This example illustrates a non-human primate model used for study of preterm labor.

The chronic vested, awake monkey has the incidence of spontaneous preterm labor and delivery similar to that observed in humans. To effectively study the effect of various agents on preterm labor, its inhibition or induction, it was necessary to assure that the model allows to continuously follow, in the awake monkey, uterine EMG to observe the frequency and strength of contractions, intrauterine pressure, maternal arterial pressure, blood flow to the uterus, as well as dynamics of the drug delivery across the placenta and drug levels on either maternal or the fetal side of placental.

Five time-mated pregnant rhesus (Macaca mulatta) monkeys having gestational ages between 106–137 days and expected term at 165 days were obtained from the California Primate Research Center.

Under general anesthesia with a halogenated agent, polyvinyl fluid-filled catheters for pressure transduction were placed in the maternal common femoral artery, the hypogastric artery, and the intra-amniotic cavity. An ultrasonic flow probe was placed around the left hypogastric artery. A polyvinyl catheter in the common femoral vein was used for infusions. All the catheters were tunneled subcutaneously to the back where they exited into a vest and steel tether system. A radiotelemeter with two electrodes was placed 1 cm apart on the uterine fundus continuously transmitted the uterine electromyogram (EMG) with a high signal-to-noise ratio.

Maternal hysterotomy for placement of monitors and catheters consistently initiated uterine irritability, usually more intense at night, which progressed to organized labor over several days. As labor progressed, the uterine EMG tracings evolved from diffuse random spikes associated with small increases in intrauterine pressure into organized, fusiform shaped complexes associated with high amplitude pressure increases. A uterine contractility index, similar to Montevideo units (*Am. J. Ob. Gyn.*, 157:1487–1495 (1987)), derived by integrating the area under the intrauterine pressure curve in 10-minute intervals was used to quantitate labor and showed that it progressively increased until the membranes ruptured and the fetus was delivered.

Active labor was induced by hysterotomy as described above or by administration of labor inducing drugs such as progestins. All monkeys were studies in the awake state after recovery from anesthesia and after confirmation of active labor by assessment of their contractility index by continuously monitoring of all variables. The progression of labor, as reflected by both electrical and mechanical activity of the uterus, was followed, as well as progression to full labor, rupture of membranes, and delivery.

In all in vivo studies, simultaneously recorded EMG's and intrauterine pressure tracings were continuously acquired in real time utilizing the LABVIEW® data flow processing software (National Instruments, Austin, Tex.) on an Apple computer. The LABVIEW® system is capable of defining the characteristics of the uterine EMG that would correlate with significant uterine contractions and excluding those waveforms that do not correlate with significant uterine contractions. The resulting data were used to monitor EMG activity to determine the strength, frequency, and severity of labor.

Short-term fetal and maternal toxicity of tested drugs was monitored by continuous assessment of both maternal and fetal physiologic parameters such as blood pressure, blood flow distribution using flow distribution using flow probes, heart rate, cardiac output, and oxygenation. The fetal hemodynamic response to various agents was assessed noninvasively by echocardiographic and Doppler ultrasound measurements of pulsatility index, cardiac contractility, and cardiac output. The long-term effect of any tested drug on fetal and neonatal growth and development was assessed by following infant monkeys that have been delivered after treatment of the mother with these drugs.

EXAMPLE 2

Determination of Inhibitory Activity of S-Nitroso-N-Acetylpenicillamine on Preterm Labor in Monkeys This example illustrates testing of various S-nitroso-N-acetylpenicillamine (SNAP) on ablation of preterm labor.

SNAP was synthesized by nitrosylation of N-acetylpenicillamine as described in *J. Pharmacol. Exp. Ther.*, 255:1256–1264 (1990).

Group 1. In the first group, four monkeys were treated as described in Example 1. When the labor contractions occurred in about 1 minute intervals reaching the uterine contractility index of about 70 mm Hg/sec., animals were either infused with SNAP (experimental animals) or with normal saline or N-acetylpenicillamine in DMSO (control animals). Infused animals received 0.5–4.0 ml/min. of 0.2 mg/ml of S-nitroso-N-acetylpenicillamine (SNAP) and corresponding for 30 minutes at a time. The infusion of SNAP at any time in the progression from uterine quiescence to full labor ablated the electromyographic and mechanical activities of the contracting uterus. The infusion of SNAP into the 4 monkeys was associated with a decrease in the frequency and strength of the contractions as seen in FIG. 3. The effect of SNAP on preterm labor was found to be dose dependent.

The vasodilatory effects of SNAP, as indicated by a decrease in mean arterial pressure, and an increase in blood flow to the uterus were also found to be dose dependent.

The monkeys were given SNAP in 30 minutes doses of 0.625–40 µg/kg/min to test its dose dependency. The greatest effects were seen at 40 µg dose.

Well-established uterine contractions were diminished or ablated. Maternal mean arterial pressure decreased in a dose dependent manner. This effect was associated with an increase in hypogastric artery flow.

No significant difference was found in the effect of SNAP whether it was infused into the systemic venous circulation via the femoral vein or whether it was administered directly into the uterine circulation via the hypogastric artery.

The infusion of normal saline or N-acetylpenicillamine dissolved in dimethyl sulfoxide had no effect on the uterine contractility index or maternal hemodynamics. Thus, SNAP-induced changes in uterine contractility and material hemodynamics are mediated through nitric oxide.

Group 2. In the second group, 5 monkeys (gestational ages 118–134 days) were treated and then administered SNAP as described above. The results of the Group 2 tests confirmed the finding that at any time in the progression from quiescent uterine to full labor, SNAP ablated the electromyographic and mechanical activities of the contracting uterus. In all 5 monkeys, the infusion of SNAP (21 occasions) was always associated with decrease in the frequency and amplitude of uterine contractions.

As above, the effect of SNAP on preterm labor was dose dependent, and the vasodilatory effect of SNAP infusion, as measured by a decrease in mean arterial pressure, and an increase in blood flow to the uterus, were also dose dependent. No significant difference was found on the effect of SNAP whether it was infused into the systemic venus circulation via the femoral vein or directly into the uterine circulation via the hypogastric artery.

EXAMPLE 3

Determination of Inhibitory Activity of Various Tocolytic Agents on Preterm Labor This example illustrates inhibitory activity of other tocolytic agents on preterm labor.

Using the monkeys and general procedure of Examples 1 and 2, two monkeys were treated with papaverine. Papaverine hydrochloride was administered to monkeys as an intravenous bolus in an amount of 6 mg/kg. This was followed by the I.V. administration of papaverine by 1 mg/kg per hour intravenous infusion. Only these extremely high doses were able to lower the uterine contractility index by 85%. Papaverine HCl was obtained from Lederle.

Zaprinast was administered to 2 monkeys using the procedures of Examples 1 and 2 in an amount of 3 mg/kg intravenous bolus decreased the uterine contractility index by 35%–95%.

Amrinone, obtained from Sanofi Winthrop Pharmaceuticals was administered to 3 monkeys in amount 0.25 mg/kg as intravenous bolus showed no significant effect of these compounds on the uterine contractility index.

EXAMPLE 4

Determination of Nitric Oxide Synthase Activity in the Pregnant Rat Uterus

This example describes methods used for in vitro studies of activity of nitric oxide synthase in pregnant rat uterine tissue.

Preparation of Uterine Tissue

Uterine tissue was obtained from time-mated pregnant female Fischer rats. Animals were euthanised by ether gas overdose. The uterus was removed, fetuses, placenta and fetal membranes were separated and discarded. Uterine tissue was rinsed several times in cold isotonic saline, minced into approximately 5 mm cubes, quick frozen in liquid nitrogen and stored at –70° C. for later determination of NOS activity. For morphological studies, a 1×1 cm sample of full thickness uterus was take prior to freezing and fixed for two hours in 4% paraformaldehyde then stored in 30% sucrose at 4° C. until processed as described below.

NOS Morphology Stains

Paraformaldehyde fixed full thickness uterine samples were examined for the presence of NOS using a tetrazolium blue dye. This method has specific for localizing NOS. Forty micron thick floating sections of the fixed tissue were incubated for 60 minutes at 37° C. in the presence of 0.5 mM nitro blue tetrazolium (NBT) dye and 1 mM NADPH. The formation of NBT formazan product required the presence of NADPH.

Measurement of NOS Enzyme Activity

NOS enzyme activity was quantitated using the [$^3$H]-arginine to [$^3$H]-citrulline conversion assay. Previously frozen minced rat uterus was homogenized using a Tissuemizer (Tekmar). Samples were suspended in a volume of 50 mM HEPES, 0.1 mM EDTA, 1 mM DTT, 1 µM leupeptin, 1 µM peptastatin (pH 7.5) that was four times the tissue's wet weight in grams. All homogenization and protein separation steps were performed at 4° C. Crude soluble and membranous subfractions were prepared from homogenates by differential centrifugation. The first centrifugation was performed at 1000 g for 20 minutes, followed by centrifugation of the supernatant at 30,000 g for 20 minutes. In all preparations, the supernatant (soluble fraction) was decanted at 30,000 g for 20 minutes. In all preparations, the supernatant (soluble fraction) was decanted from the pellet (membranous fraction). Pellets were then washed to remove residual soluble protein by resuspension in 5 ml of buffer and re-centrifugation. The final pellet was resuspended in 1 ml of buffer and re-centrifugation. The final pellet was resuspended in 1 ml of buffer. In one experiment purified cytosolic and microsomal subfractions were prepared for the purpose of demonstrating the relative proportion of NOS activity in these two subfractions, and to compare this with the crude separations. Homogenates were centrifuged at 10,000 g for 20 minutes and the resulting post-mitochondrial supernatant was subjected to ultracentrifugation at 105,000 g for 60 minutes.

Samples of the cellular subfractions (50 to 100 μg protein) were incubated at 37° C. for 45 minutes in the presence of 1 mM NADPH, 14 μm tetrahydrobiopterin, 5 μM FAD, 1 mM EGTA, 1 mM magnesium, 5 μM L-arginine and 15 nM [$^3$H]-arginine (Specific activity: 77 Ci/mmol). Calcium-sensitive NOS activity was determined by addition of 3 mM $CaCl_2$ (resulting in a total free calcium concentration of 2 mM), and 50 units bovine brain calmodulin (Calbiochem) to aminoguanidine (0.5 mM each) to the incubations. All reactions were stopped by dilution with ice cold stop buffer (5 mM HEPES, pH 5.0) and labeled citrulline was separated from labeled arginine by ion exchange chromatography on 1 ml columns of Dowex 50W-X8 (Na form) resin. [$^3$H]-citrulline was quantitated by scintillation coating (Safety Solve, Research Products, Inc.). Total protein concentration was determined using Coomassie reagent (Bio-Rad). Protein was dissolved in 1.5 N NaOH and bovine serum albumin was the standard. Enzyme activity is reported in pmol [$^3$H]-citrulline/mg protein/minute. Data are reported as means ±SE. One way ANOVA was used to evaluate differences in enzyme activity at different times in gestations, and the 95% confidence level was used.

NADPH-diaphorase Histochemical Localization of Nitric Oxide Synthase

A full thickness biopsy of the uterus was placed immediately in 2% buffered paraformaldehyde and fixed for 2 hours. The tissue then was rinsed briefly in distilled water before immersion in 30% sucrose in 0.1 M phosphate buffer (pH 7.3). The tissue may be saved at 4° C. until it is convenient to cut it. Either a cryostat or a sliding microtome was utilized for cutting sections thereof from the block. A representative 20 micron-thick section was kept and stained with Masson's trichrome for orientation later. 40 micron thick sections from each block were placed in 0.05 M Tris buffer (pH 8) in tissue culture plates. The floating tissue may be stored at 4° C. for many weeks.

For the NADPH-diaphorase reaction each section was incubated in a solution containing 1 mM NADPH/0.6 mM nitroblue tetrazolium/0.3% Triton X-100 in 0.05 M Tris buffer (pH 8) for 30 minutes. The reaction was stopped by replacing this solution with Tris buffer. The sections were rinsed for 30 minutes in Tris buffer, arranged under water on glass slides, air-dried, dehydrated in graded alcohols and mounted with Cytoseal.

All enzyme reactions containing protein were carried out at 37° C., 1 mM NADPH, tetrahydrobiopterin, FAD, Mg, 5 mM unlabelled L-arginine and 15nM $^3$H-arginine and other effectors (calmodulin and calcium) under conditions which drive the reaction at maximal velocity. For all NOS activities measured, optimal concentrations of all-cofactors were tested and the $K_m$ and $V_{max}$ for the activities were determined since these could conceivably change with gestation or hormonal conditions. Enzyme activity was expressed in pmol/min/mg protein.

The co-factors, $^3$H-arginine, and protein mixtures were incubated for 30 minutes and the reaction stopped by the addition of an iced stop buffer, pH 5.0. Controls for enzyme activity have the stop buffer added to the co-factor and protein solution before incubation. $^{14}$C-citrulline was added to the stopped samples (2 ml) to monitor column recovery. The samples were then applied to columns containing 1 ml of Dowex AG50W-X8 resin, Na$^+$ form, pre-equilibrated with 1N NaOH. Titrated citrulline was resolved from substrate arginine and quantified by scintillation counting.

The Bradford assay is used to determine the concentration of total protein in all samples using bovine serum albumin is as a standard. Enzyme activity is reported in pmol/min/mg protein.

EXAMPLE 5

Effect of Nitroglycerin on Active Labor in Sheep

This example illustrates effect of nitric oxide donor nitroglycerin on inhibition of contractions during active labor in sheep and investigates the ability of one nitric oxide donor, nitroglycerine, to inhibit uterine contractions in close-to-term laboring pregnant sheep.

Four pregnant sheep (135–140 days gestation, term 145 days) instrumented with an intra-amniotic and fetal catheters for other studies were found to be in active labor. Fetal and maternal arterial blood pressures and intra-amniotic pressure were measured with Statham P23DB pressure transducers and recorded continuously on a Gould direct-writing recorder. At least two 10-minute periods of recording of active labor were made. Nitroglycerine was then infused into a maternal vein at a rate of 1–3 μg/kg maternal weight/min until contractions ceased. If little or no effect was evident after 15 min, the infusion rate was increased to 4–6 μg/kg maternal weight/min. Once rhythmic contractions had ceased, a 10-minute recording was repeated.

The hard-copy recordings of intra-amniotic pressure of the two baseline periods during contractions and the recording during the period of uterine inactivity were scanned into a Macintosh computer and the data digitized. Sequential points, at 3-second intervals, were selected for each recording, and the mean intra-amniotic pressure (mm Hg) at that point recorded for each 200 such points during the 10-minute observation period. A mean value for the 200 observations was calculated, and this represented the overall average intra-amniotic pressure over the 10-minute period. The standard deviation for the 200 observations was calculated, and this gave an estimate of the variability of intra-amniotic pressure during the 10-minute recording period. To evaluate whether there were any differences between the variability of pressure during the two baseline period, or particularly between the period of contractions recorded immediately prior to starting the nitroglycerine infusion and the quite period during nitroglycerine infusion, the variance of the standard deviation data between the two respective periods of interest were compared by two-sided F ratio analysis in all four instances, intravenous nitroglycerine, generally in doses of 1–3 μg/kg maternal weight/min, essentially abolished the regular contractions recorded immediately before.

No differences were detected between the two periods of contraction before starting the nitroglycerine infusion. In all four animals, nitroglycerine stopped the uterine contractions. The mean intra-amniotic pressure (200 observations over 10 minutes) was 8.4 mm Hg during the period of inactivity ($p<0.05$). More importantly, the standard deviation fell from an average of 2.65 during the contraction period to 1.2 during the period of inactivity ($p<0.001$).

EXAMPLE 6

Effect of Nitroglycerin on Preterm Labor in Patients After Hysterotomy

This example illustrates the effect of nitroglycerin on preterm labor in human patients following hysterotomy and fetal surgery.

Three patients were treated with indomethacin 50 mg per rectum preoperatively to block prostaglandin synthesis before an incision was made in the uterus. Indomethacin alone had never been adequate to prevent intraoperative or postoperative contractions. Anesthesia was achieved with 0.25% halothane and nitrous oxide. Patients were hydrated overnight intravenously and then, after a light general anesthesia was induced, a central venous catheter and radial artery catheter was placed for monitoring. After the patient was anesthetized and the central venous pressure (CVP) brought to 2–6 mmHg with adequate intravenous crystalloid, a nitroglycerin drip was started and the infusion increased until mean arterial pressure began to fall indicating a physiologic endpoint. The dose range necessary to achieve a physiologic effect in three patients was from 5–15 µg/kg/min. The infusion rate was adjusted throughout the intraoperative and postoperative period to keep mean arterial pressure above 65 with an adequate volume maintained manifest by a CVP from 2–6 mmHg. The intraoperative infusion ranged from 8–20 µg/kg/min. The tone of the uterus was constantly monitored by a designated member of the surgical team, and if contractions occurred the infusion rate was increased.

Mild contractions noted at the time of uterine incision responded in all three cases to increase infusion of nitroglycerin. A radiotelemeter placed in the fetus continuously recorded fetal EKG, temperature, and amniotic fluid pressure. The fetal surgical procedures were carried out according to protocols devised for correction of fetal defects. The cystic adenomatoid malformation was resected through a thoracotomy requiring 37 minutes, and the fetal diaphragmatic hernias were repaired through a two-step incision in each case requiring two hours. Nitroglycerin infusion was continued throughout the procedure. In one case, two bolus doses of intravenous terbutaline (0.25 mg) were used at the time of uterine closure. Nitroglycerin infusion was continued during closure of the uterus and the maternal abdomen, during emergence from anesthesia and extubation in the operating room, and during transport to the Fetal Intensive Care Unit (ICU). Postoperatively uterine activity was continuously monitored by radiotelemeter recording of amniotic fluid pressure, by palpation of the maternal abdomen, and by intermittent monitoring of the gravid cervix by palpation. Direct continuous measurement of intrauterine pressure by the fetal radiotelemeter allowed not only continuous recording but also continuous calculation of a derived uterine contractility index. The contractility index which was used was calculated by integrating the area under the intraamniotic pressure curve every ten minutes, and thus reflects both the intensity and frequency of contractions.

Nitroglycerin infusion ablated essentially all uterine activity during and after hysterotomy for fetal surgery. Particularly striking was the effect of nitroglycerin infusion intraoperatively where even mild contractions were ablated by simply increasing the dose. Intraoperative nitroglycerin infusion was well-tolerated and very easy to adjust the maternal mean arterial pressure and volume status reflected by the CVP. Other than bolus doses of terbutaline used in one case, no other intraoperative tocolytic was required.

The nitroglycerin infusion was found effective intraoperatively and was continued during emergence from anesthesia, extubation, and transport to the ICU, the uterus remained quiescent. In one case, the indomethacin was continued to be administered. Administration of magnesium sulfate or terbutaline were not necessary in any of treated cases and this was confirmed by continuous monitoring by the fetal radiotelemeter device. Intrauterine pressure remained 0–2 mmHg throughout the 2–4 days that the nitroglycerin infusion was continued. The patients were alert, awake, and comfortable, the only complaint was a warm, flushed vasodilated feeling and occasion mild headache.

Nitroglycerin infusion had a positive effect on uteroplacental perfusion compared to the previous regimen because uterine artery blood flow was maintained in the vasodilated, hypervolemic state. No reversal of diastolic flow in the uterine arteries was observed. The mother remained warm and well perfused as long as maternal intravascular volume was maintained with crystalloid infusion to keep the central nervous pressure above 2 mmHg. No blood transfusions were required. There were no unexpected hemodynamic perturbations throughout an otherwise uneventful postoperative course.

When the uterus remained quite after 1–3 days, the nitroglycerin infusion was gradually weaned and nitropaste or nitroglycerin patches were substitute. The patients were discharged after six days and returned home when discharged by the physician.

EXAMPLE 7

Clinical Inhibition of Preterm Labor

This example illustrates the clinical utility of the invention in individual patient's cases. The studies are performed in strict clinical setting where the pregnant patient suffers from hysterotomy induced preterm labor which would, under untreated conditions, result in premature delivery or abortion.

Abbreviations:

NTG = nitroglycerin
OP ROOM = operating room
POD = Post operation day
POST OP = Post operation Case 1

| | |
|---|---|
| Diagnosis: | Congenital Diaphragmatic Hernia |
| Treatment: | Maternal hysterotomy and repair of hernia; partial liver resection. |

NTG Dose:

| | |
|---|---|
| OP ROOM | - 5–17 µg/kg/min IV |
| POD #0 | - 17 µg/kg/min IV |
| POD #1 | - 16–17 mcg/kg/min IV |
| POD #2 | - 16 mcg/kg/min IV |

Other Regimen:

| | |
|---|---|
| OP ROOM | - Terbutaline 0.25 mg IV two doses |
| POD #0 | - Terbutaline 0.25 mg SC at 2 µm, Indocin 50 mg PR every 4 hours |
| POD #1 | - Indocin 50 mg PR one dose; |
| POD #2 | - Indocin 50 mg PR one dose |

Results:

| | |
|---|---|
| OP ROOM | - Uterus very soft in operating room |
| Post OP | - 2–4 uterine contractions per hour; no preterm labor. |

Case 2

| | |
|---|---|
| Diagnosis: | L Congenital Diaphragmatic Hernia |
| Treatment: | Maternal hysterotomy and repair of hernia. |

NTG Dose:

| | |
|---|---|
| OP ROOM | - 10–20 μg/kg/hour IV |
| POD #0 | - 10 μG/KG/HOUR IV |
| POD #1 | - 5–10 μg/kg/hour IV |
| POD #2 | - 0–4 μg/kg/hour IV |
| Other Regimen: | |
| OP ROOM | - Terbutaline 100 μg IV 3 doses |
| POD #0 | - Indocin 25 mg every 6 hours |
| POD #1 | - Indocin 25 mg every 6 hours |
| | Terbutaline 0.25 SC one dose |
| POD #2 | - Terbutaline pump |
| | Indocin 25 mg every 6 hours |
| Results: | |
| OP ROOM | - Uterus very soft in operating room |
| Post OP | 1–3 uterine contractions per hour; |
| | no preterm labor |

Case 3

| | |
|---|---|
| Diagnosis: | L Congenital Diaphragmatic Hernia |
| Treatment: | Maternal hysterotomy and tracheal plug; |
| | attempted resection of liver. |
| NTG Dose: | |
| OP ROOM | - 1.0–12.5 μg/kg/min IV |
| POD #0 | - 9–14 μg/kg/hour IV |
| Other Regimen: | |
| OP ROOM | - Terbutaline 0.25 mg one dose |
| Results: | |
| OP ROOM | - Uterus very soft in operating room |
| Post OP | - 6–8 uterine contractions per hour; |
| | no preterm labor. |

Case 4

| | |
|---|---|
| Diagnosis: | R Congenital Cystic Adenomatoid Malformation |
| Treatment: | Maternal hysterotomy and resection of lung mass. |
| NTG Dose: | |
| OP ROOM | - 1–20 μg/kg/min IV |
| POD #0 | - 2.5–20 μg/kg/min IV |
| POD #1 | - 5–18 μg/kg/min IV |
| POD #2 | - 0–8 μg/kg/min IV |
| Other Regimen: | |
| OP ROOM | - Terbutaline 0.25 mg IV three doses |
| POD #0 | - Terbutaline 0.25 mg SC two doses |
| POD #1 | - Terbutaline 0.25 mg SC three doses |
| | Indocin 50 mg PR every 6 hours |
| POD #2 | - Indocin 50 mg PR every 6 hours |
| Results: | |
| OP ROOM | - Uterus very soft in operating room |
| Post OP | - 0–4 uterine contractions per hour |
| | no preterm labor |

Case 5

| | |
|---|---|
| Diagnosis: | L Congenital Diaphragmatic Hernia |
| Treatment: | Maternal hysterotomy and tracheal occlusion |
| NTG Dose: | |
| OP ROOM | - 20 μg/kg/min IV |
| POD #0 | - 10 μg/kg/min IV |
| POD #1 | - 1–5 μg/kg/min |
| Other Regimen: | |
| OP ROOM | - Terbutaline 0.25 mg IV one dose |
| POD #1 | - Indocin 50 mg PR every 6 hours |
| POD #2 | - Terbutaline pump |
| | Indocin 50 mg PR every 6 hours |
| Results: | |
| OP ROOM | - Uterus very soft in operating room |
| Post OP | - 0–2 uterine contractions per hour |
| | no preterm labor |

Case 6

| | |
|---|---|
| Diagnosis: | Sacrococcygeal Teratoma |
| Treatment: | Hysterotomy and resection of SCT; Fetal demise and Fetectomy |
| NTG Dose: | |
| OP ROOM | - 10 μg/kg/min IV |
| Other Regimen Results: | |
| OP ROOM | - Uterus very soft in operating room |

Case 7

| | |
|---|---|
| Diagnosis: | L Congenital Diaphragmatic Hernia |
| Treatment: | Maternal hysterotomy and repair of hernia and tracheal plug. |
| NTG Dose: | |
| OP ROOM | - 1–25 μg/kg/min IV |
| POD #0 | - 13 μg/kg/min IV |
| Other Regimen: | |
| OP ROOM Results: | - Terbutaline 0.25 mg SC one dose |
| OP ROOM | - Uterus very soft in operating room |

Case 8

| | |
|---|---|
| Diagnosis: | R Congenital Cytic Adenomatoid Malformation |
| Treatment: | Hysterotomy with resection of lung mass; fetal demise. |
| NTG Dose: | |
| OP ROOM | - 50 μg IV bolus three doses |
| | 100 μg IV bolus one dose |

Other Regimen:

Terbutaline 0.2 mg and 0.1 mg IV

Results:

Uterine contractions severe with terbutaline alone. NTG added after onset of severe palpable contractions without great effect. No nitroglycerin infusion used.

EXAMPLE 8

Physiologic and Pharmacologic Manipulation of Isolated Monkey Uterine Muscle Strips This example illustrates in vitro method used for study of monkey uterine muscle strips.

Strips of uterine muscle from gravid monkeys were studied using a tissue bath myograph system. The tissue was suspended in baths containing Krebs solution at 37° C., bubbled with 95% $O_2$/ 5% $CO_2$. Data were obtained at one-second intervals and recorded on-line via a Macintosh computer while change in tension over time and strip chart graphics were recorded using the LABVIEW® computer program.

The uterine tissue was cut into 0.5 cm×0.5 cm strips; pre-loaded in the bath with 1 gram of tension and allowed to equilibrate for one hour prior to the beginning of the experiment. All drugs were suspended in distilled water or other solvent and appropriate vehicle controls were employed. Test drugs included L-arginine, L-NMA, L-NA, NMDA, VIP, rat cGRP, SNAP, methylene blue, M&B 22948, Rolipram, and 8-bromo-cGMP, all of which effect uterine tone by modulating the nitric oxide production-cGMP stimulation muscle relaxation process.

The data were quantitated as maximal tension and integrated area (tension×time) reported as percent change from the greatest spontaneous contraction over time. These preparations were spontaneously active and were also responsive to oxytocin, bradykinin and endothelin. Electrical field stimulation may also be investigated as a non-pharmacologic means of inducing contractions.

What is claimed is:

1. A method for control, management and inhibition of a preterm labor comprising administering to a pregnant woman experiencing preterm labor before the 37th week of gestation a composition consisting essentially of a nitric oxide source capable of increasing or maintaining a level of nitric oxide in utero and decreasing the preterm labor contraction.

2. The method of claim 1 wherein the nitric oxide source is a nitric oxide donor or precursor.

3. The method of claim 2 wherein the nitric oxide source is administered orally, intravenously, subcutaneously, intravaginally, rectally, transdermally, intramuscularly, intraperitoneally, intranasally, or intraamniotically in an amount from about 1 to 1000 µg/kg body weight/day.

4. The method of claim 3 wherein the nitric oxide source is the nitric oxide donor selected from the group consisting of nitroglycerin, nitroprusside, S-nitroso-N-acetylpenicillamine, a nitric oxide nucleophile and nitric oxide adduct.

5. The method of claim 4 wherein the nitric oxide donor is administered intravenously by infusion of said donor in amount from about 1 to about 100 µg/kg/min.

6. The method of claim 5 wherein the nitric oxide donor is S-nitroso-N-acetylpenicillamine administered in an amount from about 5–20 µg/kg/minute.

7. The method of claim 5 wherein the nitric oxide donor is nitroglycerin administered in an amount from about 5–20 µg/kg/minute.

8. The method of claim 5 wherein the nitric oxide donor is diethylamino nitric oxide administered in an amount from about 5–20 µg/kg/minute.

9. The method of claim 3 wherein the nitric oxide source is the nitric oxide precursor.

10. The method of claim 9 wherein the nitric oxide precursor is L-arginine administered by infusion in an amount from about 1 to about 100 µg/kg/minute.

11. A method for control, management and inhibition of a preterm labor comprising administering to a pregnant mammal experiencing the preterm labor before its due term, a composition consisting essentially of a nitric oxide source capable of increasing or maintaining a level of nitric oxide in utero and decreasing the preterm labor contractions by at least 31%.

12. The method of claim 11 wherein the nitric oxide source is a nitric oxide donor or precursor.

13. The method of claim 12 wherein nitric oxide source is administered orally, intravenously, subcutaneously, intravaginally, rectally, transdermally, intramuscularly, intraperitoneally, intranasally, or intraamniotically in an amount from about 1 to 1000 µg/kg body weight/day.

14. The method of claim 13 wherein the nitric oxide source is the nitric oxide donor selected from the group consisting of nitroglycerin, nitroprusside, S-nitroso-N-acetylpenicillamine, a nitric oxide nucleophile and nitric oxide adduct.

15. The method of claim 14 wherein the nitric oxide donor is administered intravenously by infusion of said donor in an amount from about 1 to about 100 µg/kg/min.

* * * * *